US007585997B2

(12) United States Patent
Kashfi

(10) Patent No.: US 7,585,997 B2
(45) Date of Patent: Sep. 8, 2009

(54) COMPOUNDS AND COMPOSITIONS FOR TREATING DYSPROLIFERATIVE DISEASES, AND METHODS OF USE THEREOF

(75) Inventor: Khosrow Kashfi, Great Neck, NY (US)

(73) Assignee: Chesterford Enterprises Limited, Grand Cayman (KY)

( * ) Notice: Subject to any disclaimer, the term of this patent is extended or adjusted under 35 U.S.C. 154(b) by 498 days.

(21) Appl. No.: 11/026,757

(22) Filed: Dec. 31, 2004

(65) Prior Publication Data
US 2005/0182134 A1     Aug. 18, 2005

Related U.S. Application Data

(60) Provisional application No. 60/533,529, filed on Dec. 31, 2003.

(51) Int. Cl.
| | | |
|---|---|---|
| *C07C 69/74* | (2006.01) | |
| *C07C 69/00* | (2006.01) | |
| *C07C 69/76* | (2006.01) | |
| *C07F 9/02* | (2006.01) | |
| *C07C 203/00* | (2006.01) | |
| *C07C 303/00* | (2006.01) | |
| *C07C 241/00* | (2006.01) | |
| *C07C 233/00* | (2006.01) | |

(52) U.S. Cl. .................... 560/128; 560/8; 560/129; 558/70; 558/482; 564/80; 564/151; 564/161

(58) Field of Classification Search ................ 560/128, 560/8, 129; 558/70, 482; 564/151, 161, 564/80
See application file for complete search history.

(56) References Cited

U.S. PATENT DOCUMENTS
4,920,129 A  *  4/1990  Shiokawa et al. ........... 514/300

FOREIGN PATENT DOCUMENTS
| EP | 04 81 5885 SR | 9/2007 |
|---|---|---|
| WO | WO 00/44705 A | 8/2000 |
| WO | WO 03/013499 A | 2/2003 |
| WO | WO 03/013499 A2 * | 2/2003 |
| WO | WO 03/084550 A | 12/2007 |

OTHER PUBLICATIONS

Yamanaka et al (Yakugaku Zasshi (1968), 88(1), 116-117).*
Database CA [Online] Chemical Abstracts Service, Columbus, OH, US; Asakawa, Hiroyuki et al: "Chemistry of salicylic acid and anthranilic acid. I. Reduction of methyl salicylate, methyl anthranilate, and their derivatives with sodium borohydride" XP002451582 Database accession No. 1979:491311 *abstract*.
Database CA [Online] Chemical Abstracts Service, Columbus, OH, US; "Preparation of (dihydroxyphenyl) acrylamide derivatives and compositions containing coloring agents" XP002451583 Database accession No. 2001:729677.
Database Crossfire Beilstein Belstein Institut Zur Foerderung Der Chemischen Wissenchaften, Frankfurt Am Main, DE; XP002451584 Database accession No. 7925516 *abstract*.

* cited by examiner

*Primary Examiner*—Jafar Parsa
(74) *Attorney, Agent, or Firm*—The Farrell Law Firm, LLP

(57) ABSTRACT

Compounds are disclosed with activity towards killing dysproliferative cells in vitro and treating cancer in vivo. Cancers such as cancer of the colon, pancreas, prostate, lung, breast, urinary bladder, skin and liver are exemplary. Compounds, pharmaceutical compositions and methods of use are described.

4 Claims, 8 Drawing Sheets

COMPOUNDS AND COMPOSITIONS FOR TREATING DYSPROLIFERATIVE DISEASES, AND METHODS OF USE THEREOF

CROSS-REFERENCE TO RELATED APPLICATION

This application claims priority to provisional application Ser. No. 60/533,529, filed Dec. 31, 2003, which is incorporated herein by reference in its entirety.

FIELD OF THE INVENTION

The invention is directed to compounds that inhibit the growth of dysproliferative cells and can be used to treat cancer. The invention is further directed to the synthesis and uses for said compounds as well as compositions comprising said compounds.

BACKGROUND OF THE INVENTION

Dysproliferative diseases including neoplasms such as cancer remain a major health problem accounting for significant morbidity and mortality in the US and nearly all of the rest of the world. Despite substantial progress in the last two decades, there remain many cancers for which currently available methods are either partially or totally ineffective. Thus novel agents or methods are needed either to prevent the development of cancer, or, in the case where neoplasia has already developed, to render the host organism cancer-free or to reduce its neoplastic burden to a level compatible with life or at least to facilitate the use of concomitant therapies.

There has been significant progress in understanding the fundamental processes underlying the development of neoplasia. In its essence, neoplasia, including cancer, can be viewed as the inappropriate accumulation of cells, in violation of the exquisite balance between cell renewal and cell death. For neoplasia to develop, either cell renewal must be increased or cell death decreased or both. A corollary to this relationship is that an agent that affects these processes favorably for the host organism (and, consequently, unfavorably for the neoplasm), is a potential antineoplastic drug.

One approach to develop new antineoplastic agents is to synthesize novel chemical compounds and screen them for their effect on cell growth. This is achieved by determining the number of a given set of cells following their exposure to the agent under evaluation and comparing it to that of untreated control cells. For an agent to have antineoplastic properties, it must inhibit the growth of neoplastic cells compared to untreated control, so that its sustained or repeated application will progressively diminish the tumor mass, ultimately leading to the extinction of neoplasia. It is also a logical extension of these considerations that other diseases such as, for example, psoriasis in which cell kinetic abnormalities, in other words abnormalities in cell renewal or cell death, contribute to their pathogenesis, will be amenable to treatment by such agents.

It is toward the identification of novel compounds with antineoplastic properties, and the identification of unexpected antineoplastic activity in compounds otherwise known in the art, that the present application is directed.

All citations in the present application are incorporated herein by reference in their entireties. The citation of any reference herein should not be construed as an admission that such reference is available as "Prior Art" to the instant application.

SUMMARY OF THE INVENTION

As discussed above, there remains a need for the development of new therapeutics capable of inhibiting the growth of dysproliferative cells. In a first aspect, the present invention provides compounds of general Formula I:

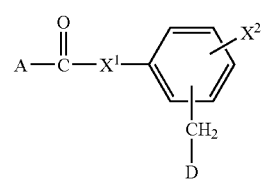

Formula (I)

or a tautomer thereof, or a prodrug, salt, hydrate or ester thereof;

wherein $X^1$ is selected from the group consisting of —O— and —NH—;

wherein $X^2$ is one or more substituents independently selected from the group consisting of hydrogen, halogen, hydroxyl, —$NO_2$, —$ONO_2$, —CN; an optionally substituted aliphatic, alicyclic, heteroaliphatic, heterocyclic, aromatic, heteroaromatic moiety; —$OR^R$, —$S(=O)_nR^d$, —$NR^bR^c$, —$C(=O)R^a$ and —$C(=O)OR^a$;

wherein n is 0-2, $R^R$ is an optionally substituted aliphatic, alicyclic, heteroaliphatic, heterocyclic, aromatic, heteroaromatic or acyl moiety;

$R^a$, for each occurrence, is independently selected from the group consisting of hydrogen and an optionally substituted aliphatic, alicyclic, heteroaliphatic, heterocyclic, aromatic, or a heteroaromatic moiety;

$R^b$ and $R^c$, for each occurrence, are independently selected from the group consisting of hydrogen; hydroxy; $SO_2R^d$; and aliphatic, alicyclic, heteroaliphatic, heterocyclic, aromatic, heteroaromatic or an acyl moiety;

$R^d$, for each occurrence, is independently selected from the group consisting of hydrogen; —$N(R^e)_2$; aliphatic, aryl and heteroaryl; and $R^e$, for each occurrence, is independently hydrogen or aliphatic;

wherein A is an optionally substituted aliphatic, alicyclic, heteroaliphatic, heterocyclic, aromatic, or heteroaromatic group such as but not limited to those moieties described in further detail herein below;

wherein D is hydroxyl; nitrate; halide; tosylate; phosphate; —$OSO_2NR_xR_y$, where $R_x$ and $R_y$ are independently hydrogen, or an aliphatic, alicyclic, heteroaliphatic, heterocyclic, aromatic, heteroaromatic or acyl moiety; —O—$C_6H_4OC(=O)CH_3$; an alkoxy moiety; an acyl moiety; or

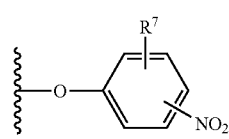

Formula (II)

where $R^7$ is hydrogen or one or more nitro groups.

In one embodiment, A is

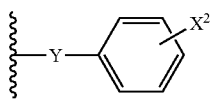

Formula (III)

wherein $X^2$ is one or more substituents as defined above, and Y is $(—C—)_n$, wherein n is 0 to 4, optionally containing one or more unsaturated bonds in the $(—C—)_n$ moiety when n is 2 or greater.

In another embodiment, A is among moieties including but not limited to:

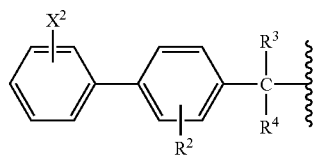

Formula (IV)

wherein $X^2$ is one or more substituents as described above, $R^2$ is at least one halogen, and $R_3$ and $R_4$ are independently hydrogen or an aliphatic group; or

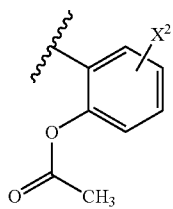

Formula (V)

wherein $X^2$ is one or more substituents as described above;

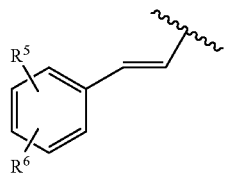

Formula (VI)

where $R^5$ and $R^6$ are independently hydrogen, —OH, alkoxy, halide, trifluoroalkyl, alpha-haloalkyl, trifluoroalkoxy, or $R^a$ as described above; or

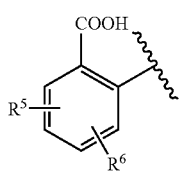

Formula (VII)

wherein $R^5$ and $R^6$ are independently as described above; or wherein A is a straight chain or branched aliphatic moiety.

In a further aspect, the invention is directed to compositions comprising compounds of formula (I), as described generally herein. In a specific embodiment, the compositions are pharmaceutical compositions which are useful in the treatment of human and animal dysproliferative diseases including neoplasms and cancer, including their benign and malignant forms and also in the prevention of the development of human and animal neoplasias and in the treatment of diseases characterized by abnormal cellular proliferation but not neoplastic per se, such as, for example, psoriasis. Such compositions can comprise one or more other pharmaceutical agents in addition to one or more compounds of the invention.

In another embodiment, the invention is directed to a method for inhibiting or blocking the growth of dysproliferative cells in a subject in need thereof by administering to said subject an amount of the compound or composition of the present invention effective to inhibit or block growth of said dysproliferative cells. The subject may be a human patient or animal.

In yet another aspect, the present invention provides methods for treating any disorder related to abnormal cell growth comprising administering to a subject (e.g., human patient or animal) in need thereof a therapeutically effective amount of a compound of formula (I) of the invention or a pharmaceutical composition comprising a compound of the invention. In a preferred embodiment, the disorder is a dysproliferative disease, more preferably neoplasia and most specifically cancer.

The compounds of the present invention may be used for the manufacture of a medicament for treatment of a dysproliferative disease.

The invention is further directed to methods for synthesizing said compounds. These methods include
a) reacting an aliphatic or aromatic carboxylic acid with thionyl chloride to obtain an acid chloride;
b) reacting the acid chloride of a) with para-, or ortho-, or meta-hydroxy benzaldehyde to obtain said compound;
c) and isolating said compound.

The compound of b) may be reduced to obtain an alcohol. The alcohol maybe converted to a halogenated compound. The halogenated compound may be nitrated to obtain a nitrated compound.

BRIEF DESCRIPTIONS OF THE DRAWINGS

DEFINITIONS

Figure 1:
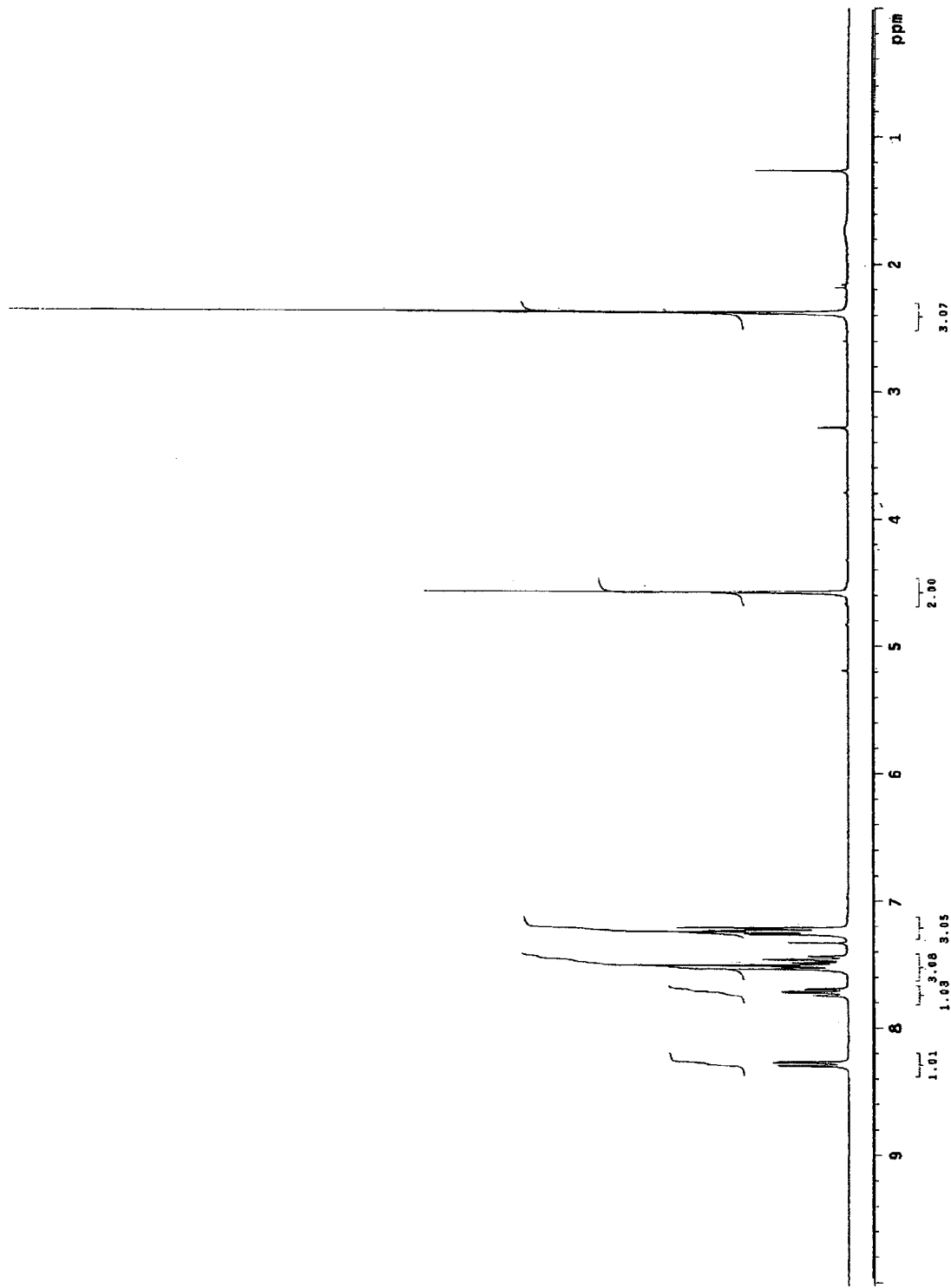
FIG. 1 shows an NMR spectrum of 2-(acetyloxy)benzoic acid 4-(bromomethyl)phenyl ester (Compound 38).
Figure 2:
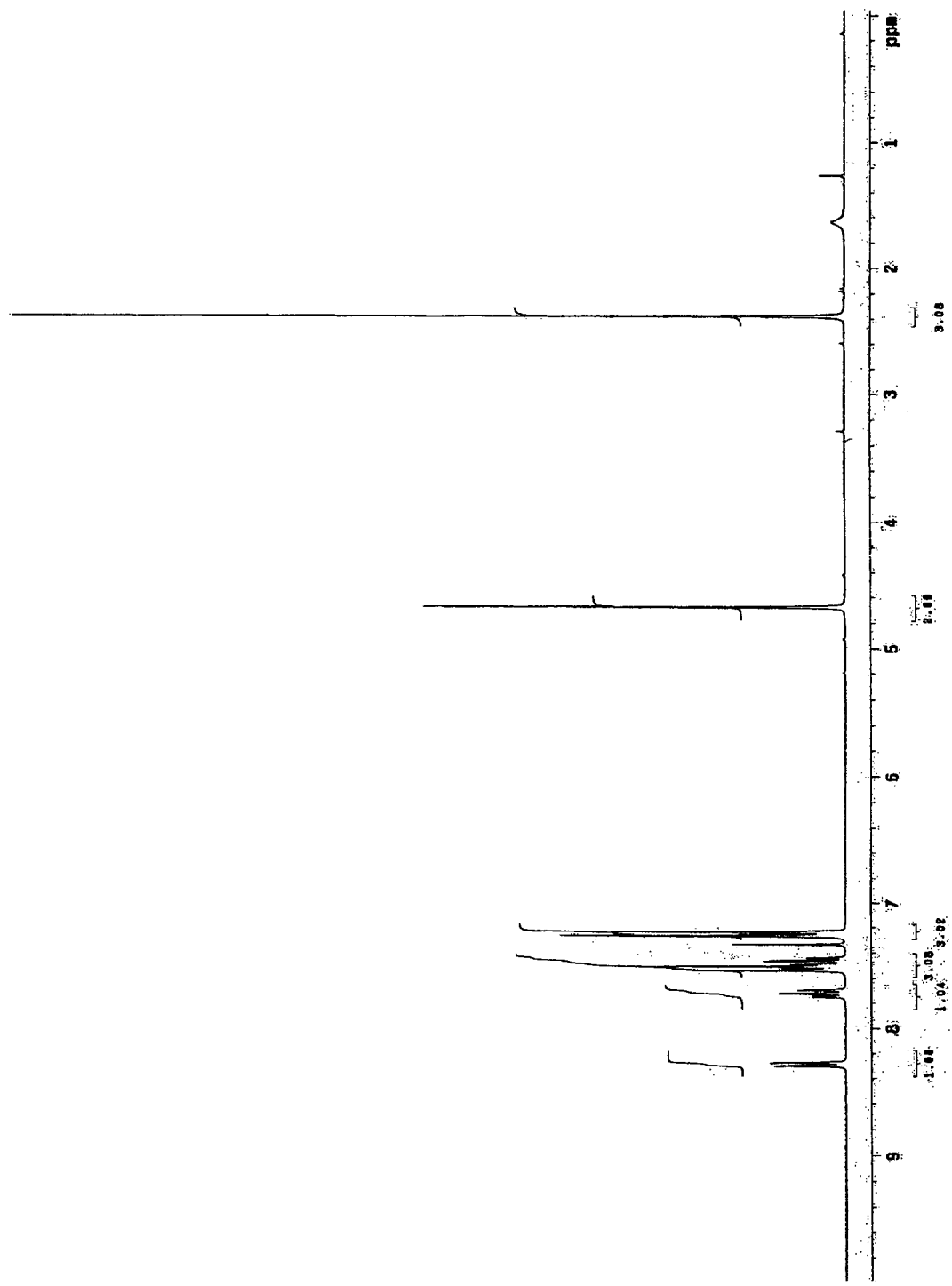
FIG. 2 shows an NMR spectrum of 2-(acetyloxy)benzoic acid 4-(chloromethyl)phenyl ester (Compound 35).

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, and alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds, which combine the properties of aliphatic and cyclic compounds and include but are not limited to monocyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl, cyclohexyl, —$CH_2$-cyclohexyl, cyclohexenylethyl, cyclohexanylethyl, norborbyl moieties and the like, which again, may bear one or more substituents.

The term "alkoxy" or "alkyloxy", as used herein refers to a saturated (i.e., O-alkyl) or unsaturated (i.e., O-alkenyl and O-alkynyl) group attached to the parent molecular moiety through an oxygen atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, i-butoxy, sec-butoxy, tert-butoxy, neopentoxy, n-hexoxy and the like.

The term "alkylthio" or "thioalkyl" as used herein refers to a saturated (i.e., S-alkyl) or unsaturated (i.e., S-alkenyl and S-alkynyl) group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of thioalkyl include, but are not limited to, methylthio, ethylthio, propylthio, isopropylthio, n-butylthio, and the like.

The term "alkylamino" refers to a group having the structure —$NHR'$ wherein R' is alkyl, as defined herein. The term "aminoalkyl" refers to a group having the structure $NH_2R'$—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —$ONO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of R independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted. Additional examples of generally applicable substituents are illustrated by the specific embodiments shown in the Examples that are described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaromatic moiety", as used herein, refers to a stable mono- or polycyclic, unsaturated moiety having preferably 3-14 carbon atoms, each of which may be substituted or unsubstituted; and comprising at least one heteroatom selected from O, S and N within the ring (i.e., in place of a ring carbon atom). In certain embodiments, the term "heteroaromatic moiety" refers to a planar ring comprising at least one heteroatom, having p-orbitals perpendicular to the plane of the ring at each ring atom, and satisfying the Huckel rule where the number of pi electrons in the ring is (4n+2) wherein n is an integer.

It will also be appreciated that aromatic and heteroaromatic moieties, as defined herein may be attached via an alkyl or heteroalkyl moiety and thus also include -(alkyl)aromatic, -(heteroalkyl)aromatic, -(heteroalkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl", as used herein, does not differ significantly from the common meaning of the term in the art, and refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkyiheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7- membered ring or a polycyclic group herein at least one ring atom is a heteroatom selected from O, S and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein.

The terms "halo" "halide" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—NH$_2$), secondary (—NHR$_x$), tertiary (—NR$_x$R$_y$) or quaternary (—N$^+$R$_x$R$_y$R$_z$) amine, where R$_x$, R$_y$ and R$_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "acyl", as used herein, refers to a group having the general formula —C(=O)R, where R is an aliphatic, alicyclic, heteroaliphatic, heterocyclic, aromatic or heteroaromatic moiety, as defined herein.

The term "sulfonamido", as used herein, refers to a group of the general formula —SO$_2$NR$_x$R$_y$, where R$_x$ and R$_y$ are independently hydrogen, or an aliphatic, alicyclic, heteroaliphatic, heterocyclic, aromatic, heteroaromatic or acyl moiety, as defined herein.

The term "benzamido", as used herein, refers to a group of the general formula PhNR$_x$—, where R$_x$ is hydrogen, or an aliphatic, alicyclic, heteroaliphatic, heterocyclic, aromatic, heteroaromatic or acyl moiety, as defined herein.

The term "C$_{1-6}$alkylidene", as used herein, refers to a substituted or unsubstituted, linear or branched saturated divalent radical consisting solely of carbon and hydrogen atoms, having from one to six carbon atoms, having a free valence "-" at both ends of the radical.

The term "C$_{2-6}$alkenylidene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle"and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains at least one additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Compounds of the invention may be considered prodrugs as both the ester or amide linkage adjacent to substituent A, and leaving group D, generate quinone intermediates that kill dysproliferative cells. Certain exemplary pharmaceutical compositions and pharmaceutically acceptable derivatives will be discussed in more detail herein below.

By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

DETAILED DESCRIPTION OF THE INVENTION

The present invention discloses compounds and pharmaceutical compositions thereof that possess anti-dysproliferative activities and in particular antineoplastic properties based on their ability to inhibit the growth of dysproliferative cells, be they benign or malignant. While Applicant has no duty of disclosure of the mechanism by which the compounds of the invention are believed to operate, and is not bound in any way thereby, the Applicant, initially seeking to modify naturally occurring compounds such as cinnamic acid, observed that nitration of such compounds, compared to their respective parent compounds, enhanced their biological activity with respect to their ability to inhibit the growth of cancer cells. Furthermore, the Applicant, while studying said nitrated derivatives of naturally occurring compounds, such as cinnamic acid 4-(nitroxymethyl)phenyl ester, made the surprising and unexpected discovery that the role of —ONO$_2$ in the anticancer activity of this molecule was that of a leaving group (as is known to persons skilled in the chemical arts), and that by replacing the —ONO$_2$ group with other members of the known class of leaving groups with different properties, the biological activity of the molecule could still be enhanced. Novel compounds bearing —OH, —Cl or —Br instead of —ONO$_2$ had IC$_{50}$s for cell growth inhibition reflecting their relative rank with respect to their ability to function as leaving groups. Contrary to the teachings in the art that the —ONO$_2$ group per se is important for said biological activity, Applicant discovered that it is other properties of the compounds disclosed herein that make them powerful compounds against dysproliferative cells, including neoplastic cells and cancer cells.

The compounds of the invention include compounds of the general formula (I) as defined below:

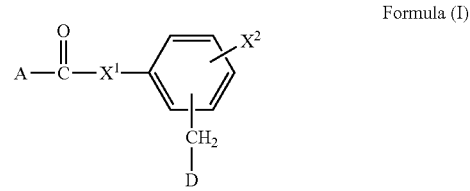

Formula (I)

or a tautomer thereof, or a prodrug, salt, hydrate or ester thereof;

wherein $X^1$ is selected from the group consisting of —O— and —NH—;

wherein $X^2$ is one or more substituents independently selected from the group consisting of hydrogen, halogen, hydroxyl, —NO$_2$, —ONO$_2$, —CN; an optionally substituted aliphatic, alicyclic, heteroaliphatic, heterocyclic, aromatic, heteroaromatic moiety; —OR$^R$, —S(=O)$_n$R$^d$, —NR$^b$R$^c$, —C(=O)R$^a$ and —C(=O)OR$^a$;

wherein n is 0-2, R$^R$ is an optionally substituted aliphatic, alicyclic, heteroaliphatic, heterocyclic, aromatic, heteroaromatic or acyl moiety;

R$^a$, for each occurrence, is independently selected from the group consisting of hydrogen and an optionally substituted aliphatic, alicyclic, heteroaliphatic, heterocyclic, aromatic, or a heteroaromatic moiety;

R$^b$ and R$^c$, for each occurrence, are independently selected from the group consisting of hydrogen; hydroxy; SO$_2$R$^d$; and aliphatic, alicyclic, heteroaliphatic, heterocyclic, aromatic, heteroaromatic or an acyl moiety;

R$^d$, for each occurrence, is independently selected from the group consisting of hydrogen; —N(R$^e$)$_2$;

aliphatic, aryl and heteroaryl; and

R$^e$, for each occurrence, is independently hydrogen or aliphatic;

wherein A is an optionally substituted aliphatic, alicyclic, heteroaliphatic, heterocyclic, aromatic, or heteroaromatic group such as but not limited to those moieties described in further detail herein below;

wherein D is hydroxyl; nitrate; halide; tosylate; phosphate; —OSO$_2$NR$_x$R$_y$, where R$_x$ and R$_y$ are independently hydrogen, or an aliphatic, alicyclic, heteroaliphatic, heterocyclic, aromatic, heteroaromatic or acyl moiety; —O—C$_6$H$_4$OC (=O)CH$_3$; an alkoxy moiety; an acyl moiety; or

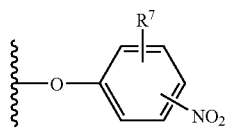

Formula (II)

where $R^7$ is hydrogen or one or more nitro groups.

The compounds of Formula I are not limited by the position of the substituents on the aromatic ring. The —$CH_2$-D moiety may be meta, ortho or para to the A-C(=O)—$X^1$ moiety, in particular when $X^2$ is H. If one or more $X^2$ substituents are present, they may be positioned at any unoccupied position(s). Thus, any and all positional isomers of compounds of Formula I are embraced by the invention. As will be apparent from the further discussion below on synthetic methods for the compounds of the invention, the A-C(=O)—$X^1$— moiety is facilely derived from a carboxylic acid-containing reactant (A-C(=O)—OH) or an amide-containing reactant (A-C(=O)—NH), and thus the A-C(=O)—$X^1$— moiety may be referred to herein as being derived from a compound with the structure A-C(=O)—OH or A-C(=O)—NH.

In one embodiment of compounds of Formula (I) of the invention, A is

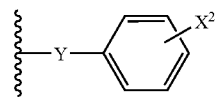

Formula (III)

wherein $X^2$ is one or more substituents as defined above, and Y is (—C—)$_n$, wherein n is 0 to 4, and when C is 2 or more, Y optionally contains one or more unsaturated bonds. For example, when n=0, the optionally substituted aromatic ring is bonded to the —C(=O)—$X^1$— substituent of Formula (I). When n=1, Y is —$CH_2$—. When n=2, Y may be —$CH_2$—$CH_2$—, —CH=CH— or ethynyl radical. When n=3, Y may be —$CH_2$—$CH_2$—$CH_2$—, an allyl radical, —CH=CH—$CH_2$— or —$CH_2$—CH=CH—, or a triple bond within the radical. When n=4, the divalent radical may have any combination of saturation and unsaturation.

Among the preferred but non-limiting selections of substituent A of Formula I, in a first embodiment, A is derived from among non-steroidal anti-inflammatory drugs (NSAIDs) including but not limited to aspirin or formula IV or an analog of either of the foregoing.

Suitable analogs of formula IV include but are not limited to derivatives with one or more fluorine atoms substituted on one or both of the benzene rings of the formula IV moiety; and compounds with one or more substitutions on the alpha carbon, such as ethyl, dimethyl, diethyl, propyl and other such aliphatic substitutions. Thus, in one embodiment, A may be

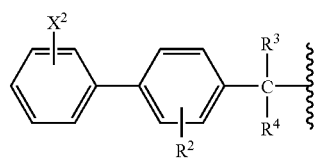

Formula (IV)

wherein $X^2$ is one or more substituents as described above, $R^2$ is at least one halogen, and $R_3$ and $R_4$ are independently hydrogen or an aliphatic group. In a preferred embodiment, $R^2$ is F. In a more preferred embodiment, $X^2$ is H, $R^2$ is F (at position 3 relative to $CR^3R^4$) and $R^3$ and $R^4$ are H and $CH_3$, respectively.

Thus, in one preferred but non-limiting embodiment, A can be

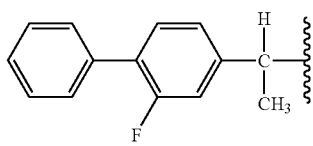

Formula (IVa)

In a second embodiment, A is derived from aspirin, such as shown below:

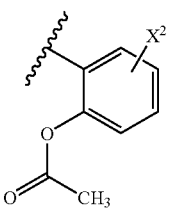

Formula (V)

where $X^2$ is one or more substituents as described above. In a preferred but non-limiting embodiment, A is

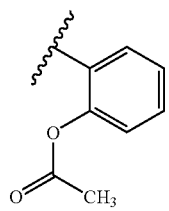

Formula (Va)

In a third embodiment, A is derived from cinnamic acid, or an analog of cinnamic acid, such as is shown below:

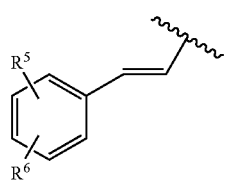

Formula (VI)

where $R^5$ and $R^6$ are independently hydrogen, —OH, alkoxy, halide, trifluoroalkyl, alpha-haloalkyl, trifluoroalkoxy, or $R^a$ as described above. Non-limiting examples of the foregoing include trifluoromethyl, alpha-fluoromethyl, 4-(anisylideneamino), 2-(hexadecyloxy), and 4-nitro-alpha-(ortho-tolyl). Examples of Formula VI from which group A in Formula I can be selected include but are not limited to 3,4-dihydroxy, o-, m- and p-hydroxy; 2,3-dihydroxy; 3,5-dihydroxy; 3,4- dimethoxy; 3-hydroxy-4-methoxy and 3,4-dimethoxy. Thus, A can be

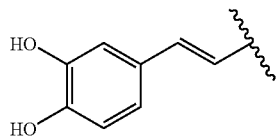

Formula (VIa)

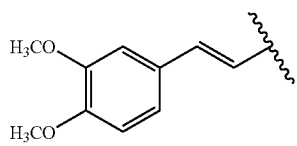

Formula (VIb)

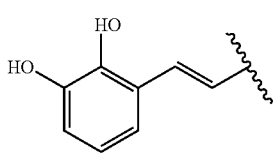

Formu;la (VIc)

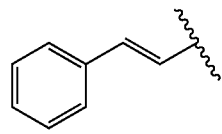

Formula (VId)

In another embodiment, A is derived from phthalic acid, or an analog of phthalic acid, as shown below

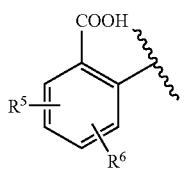

Formula (VII)

wherein $R^5$ and $R^6$ are as described above. Examples of such A moieties include:

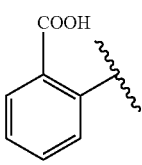

Formula (VIIa)

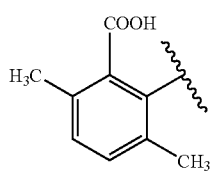

Formula (VIIb)

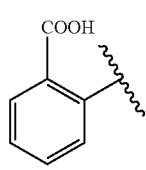

Formula (VIIc)

In yet a further embodiment, A is a straight chain or branched aliphatic moiety, preferably 1 to 7 carbons. In compounds wherein A is an aliphatic group, $X^2$ is preferably a moiety derived from the esterification of resveratrol or an analog thereof to a carboxylic acid on the aromatic ring, i.e. $X^2$ is (—C=O)$OR^a$. Suitable analogs of resveratrol include but are not limited to the compounds described by She Q-B et al. in Oncogene, volume 22, pp 2143-2150, 2003, and in the publication by Roberti et al. in J. Med Chem, volume 46, pp 3546-3554, 2003. In one embodiment, $X^2$ is

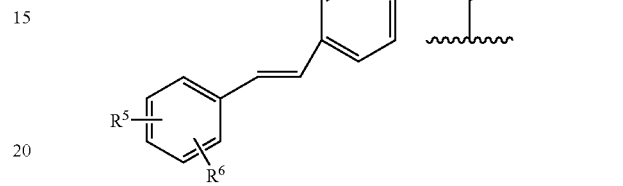

(VIII)

wherein $R^5$ and $R^6$ are as described above.

Non-limiting selections of $X^2$ are thus, by way of non-limiting examples,

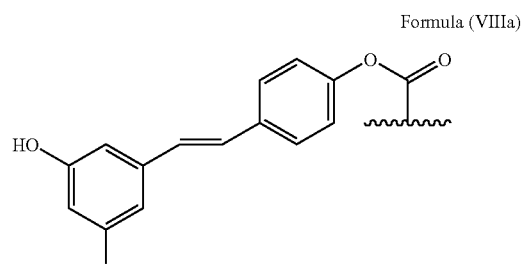

Formula (VIIIa)

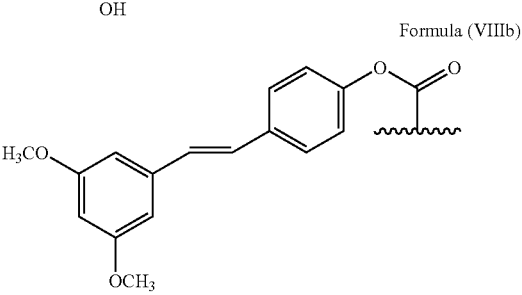

Formula (VIIIb)

In a preferred embodiment of the foregoing, A is methyl.

In addition to the foregoing selections of A, also embraced by the invention are compounds of Formula I wherein A is selected from the group consisting of an optionally substituted aliphatic, alicyclic, heteroaliphatic, aromatic, heterocyclic or heteroaromatic moiety.

The D substituent of Formula I is selected from among a hydroxyl moiety;

a nitrate moiety: —$ONO_2$;

a halide moiety, such as F, Cl, or Br.

a tosylate moiety;

a phosphate moiety: —$OPO_3$;

an —O-sulfonamide of formula —$OSO_2NR_xR_y$, where $R_x$ and $R_y$ are independently hydrogen, or an aliphatic, alicyclic, heteroaliphatic, heterocyclic, aromatic, heteroaromatic or acyl moiety such as but not limited to N,N-dimethyl-O-sulfonamide or N-ethyl-N-methyl-O-sulfonamide;

—O—C$_6$H$_4$(p)OC(=O)CH$_3$;

an —O-aromatic nitro compound of Formula II below:

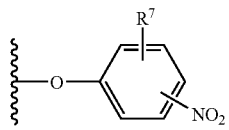

Formula (II)

wherein R$^7$ is hydrogen or one or more nitro groups, such that Formula II can be but is not limited to p-nitrophenoxy or 2,4-dinitrophenoxy;

an aliphatic acyl moiety such as acetyl, propionyl; an acyl moiety with a longer aliphatic chain as defined herein;

an alkoxy group, such as methoxy, ethyloxy, propyloxy, or an alkoxy moiety with a longer aliphatic chain as defined herein;

As noted above, the substituent containing the aforementioned D moiety, —CH$_2$—D, may be at any location on the benzene ring relative to the position of the —X$_1$—C(=O)—A substituent, i.e., meta, ortho or para thereto. The invention embraces all such positional isomers.

The selections among substituent X$^2$ are as described above. As mentioned above, in certain cases where A is an aliphatic group such as methyl, X$^2$ may be a carboxylic acid to which an alcohol or polyphenol is esterified, such as resveratrol or an analog thereof. Suitable analogs of resveratrol include but are not limited to the compounds described by She Q-B et al. in Oncogene, volume 22, pp 2143-2150, 2003, and in the publication by Roberti et al. in J. Med Chem, volume 46, pp 3546-3554, 2003. Other preferred examples of X$^2$ include one or more —OH, —OCH$_3$, or —F, at one or more positions not occupied by the substituents containing moieties A and D. Other preferred examples of X$^2$ include —CH$_3$, and —C$_2$H$_5$.

Thus, based on the selections of substituents described above, among the various non-limiting examples of compounds of the invention derived from flurbiprophen include where m-, o-, and p- as shown below refer to the corresponding meta-, ortho-, and para-isomers, respectively, of the indicated compounds:

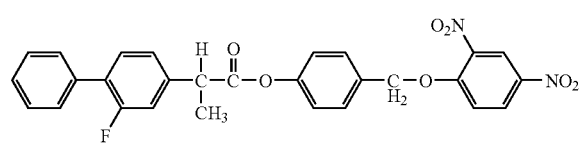

Compound 1

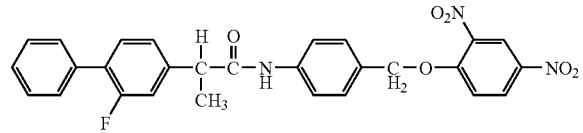

Compound 2

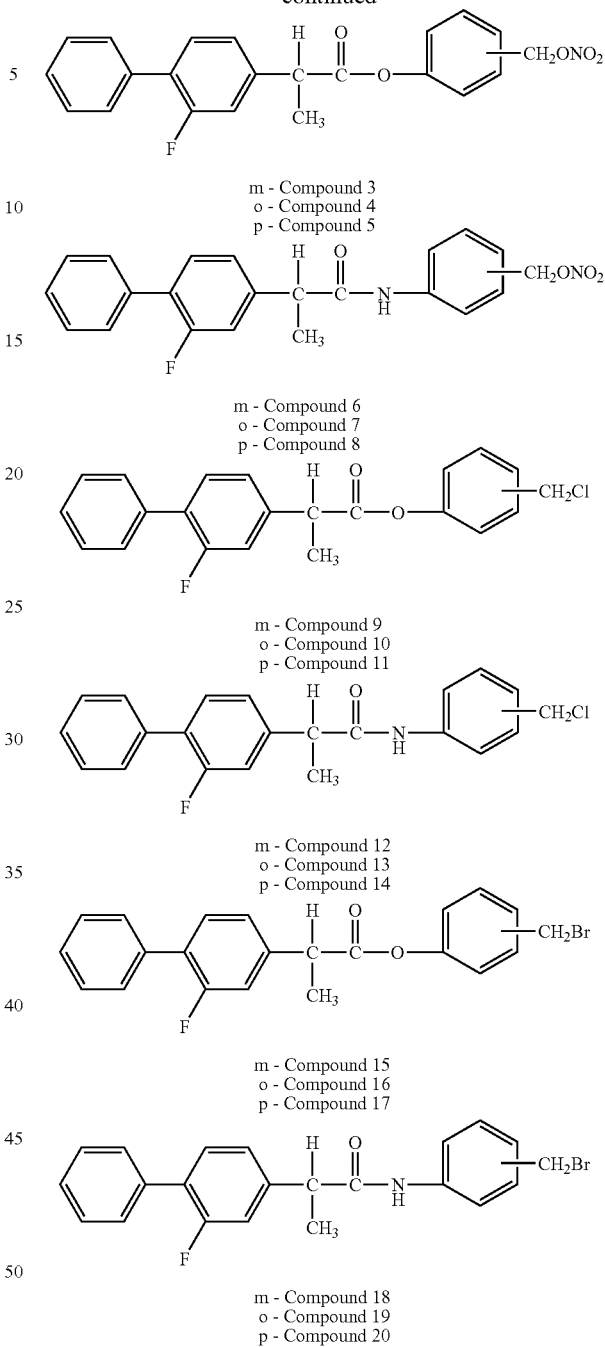

Compounds of the invention derived from aspirin include but are not limited to:

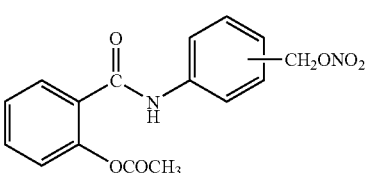

m - Compound 21
o - Compound 22
p - Compound 23

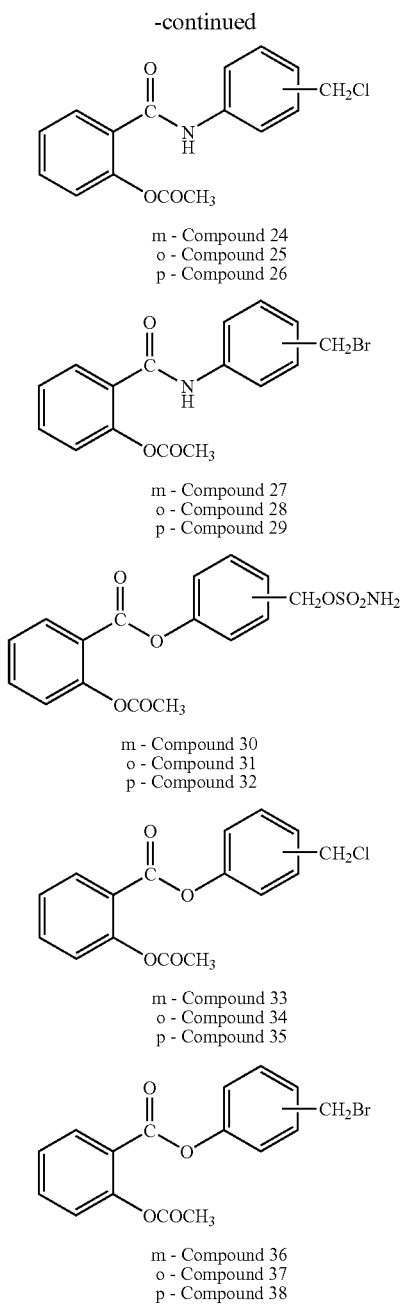

m - Compound 24
o - Compound 25
p - Compound 26 m - Compound 27
o - Compound 28
p - Compound 29 m - Compound 30
o - Compound 31
p - Compound 32 m - Compound 33
o - Compound 34
p - Compound 35 m - Compound 36
o - Compound 37
p - Compound 38

Compounds of the invention comprising caffeic acid include but are not limited to:

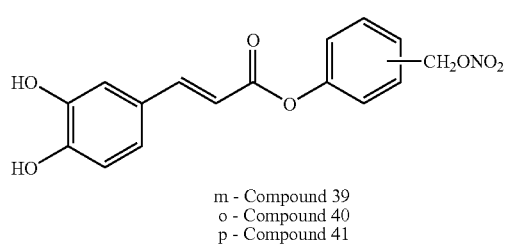

m - Compound 39
o - Compound 40
p - Compound 41

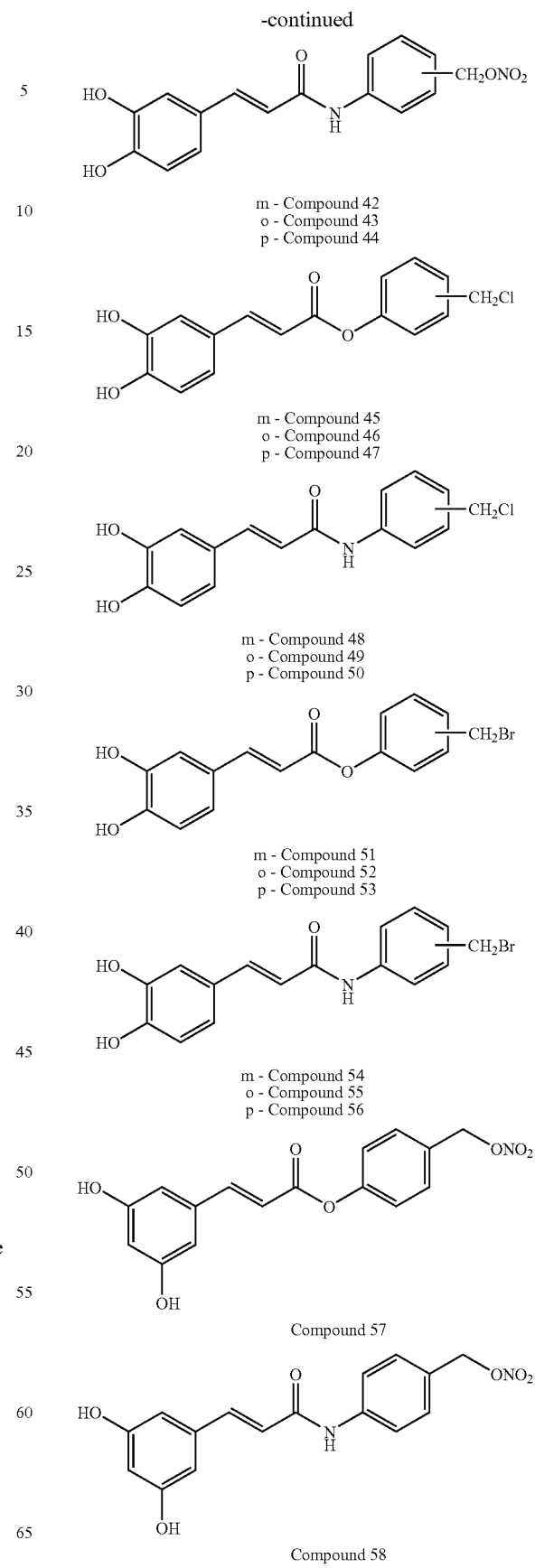

m - Compound 42
o - Compound 43
p - Compound 44 m - Compound 45
o - Compound 46
p - Compound 47 m - Compound 48
o - Compound 49
p - Compound 50 m - Compound 51
o - Compound 52
p - Compound 53 m - Compound 54
o - Compound 55
p - Compound 56

Compound 57

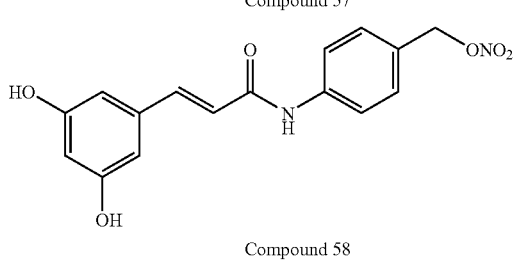

Compound 58

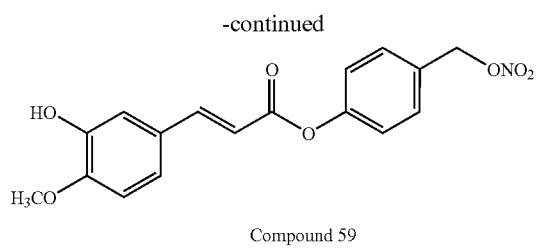

Compound 59

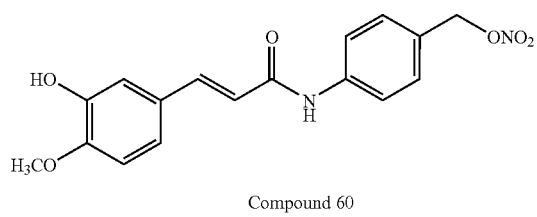

Compound 60

Compounds of the invention comprising cinnamic acid include but are not limited to:

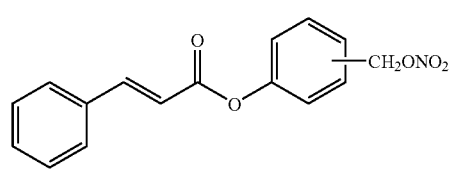

m - Compound 61
o - Compound 62
p - Compound 63

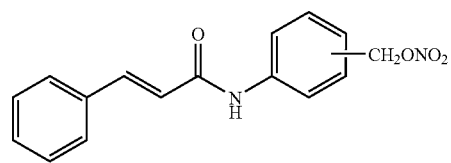

m - Compound 64
o - Compound 65
p - Compound 66

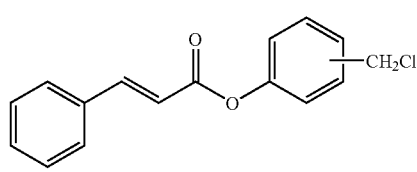

m - Compound 67
o - Compound 68
p - Compound 69

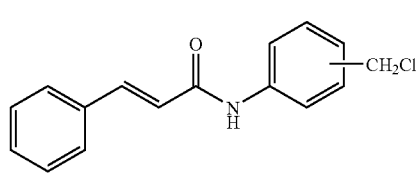

m - Compound 70
o - Compound 71
p - Compound 72

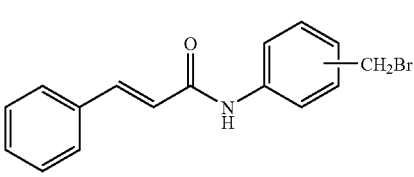

m - Compound 73
o - Compound 74
p - Compound 75

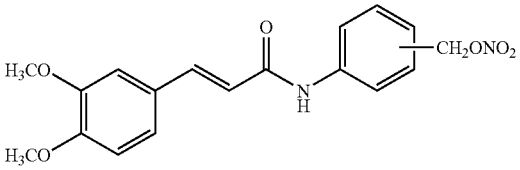

m - Compound 76
o - Compound 77
p - Compound 78

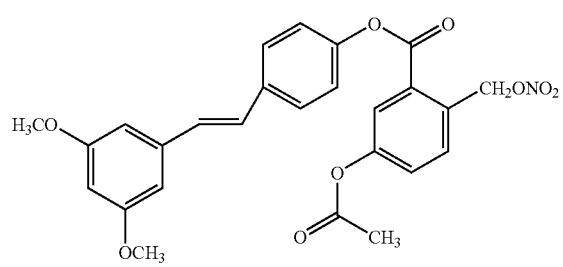

Compounds of the invention derived from when A-C(=O)OH is acetic acid (i.e., A=CH$_3$—) and R$^2$ is Formula (VIII) include but are not limited to:

Compound 85

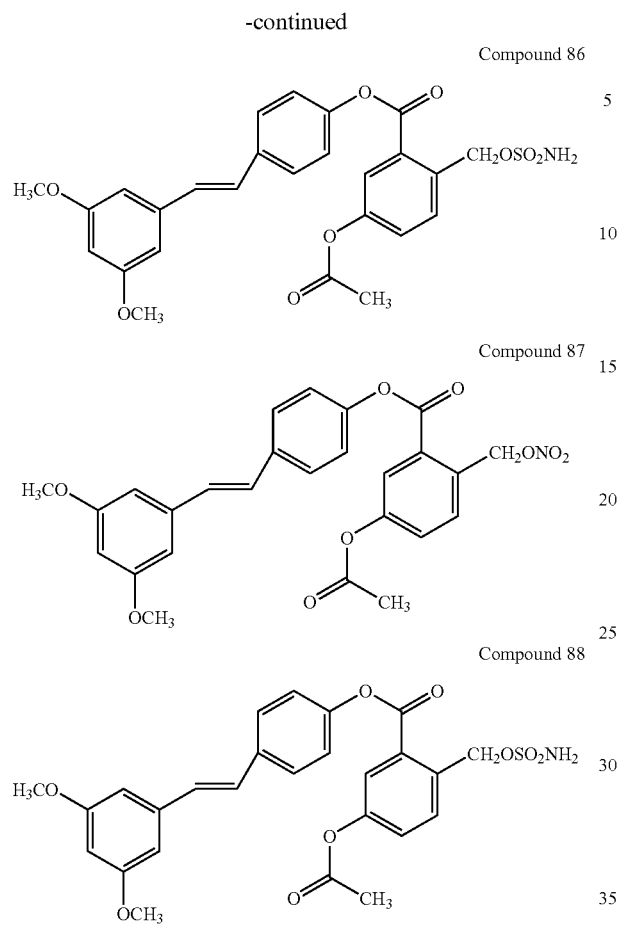

Compounds of the invention comprising a phthalic acid include but are not limited to:

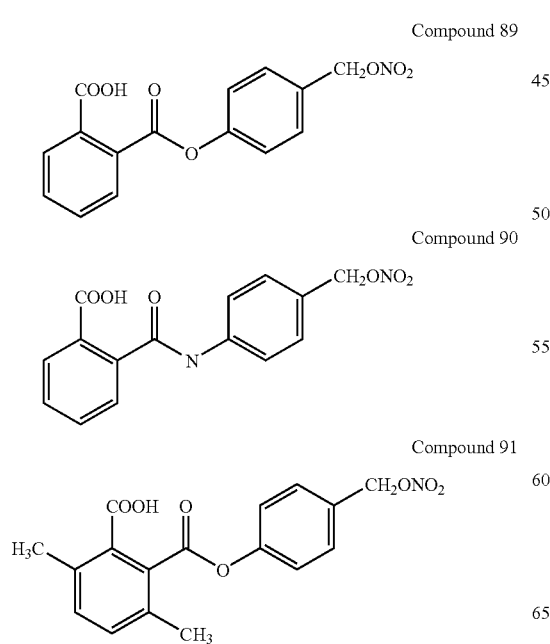

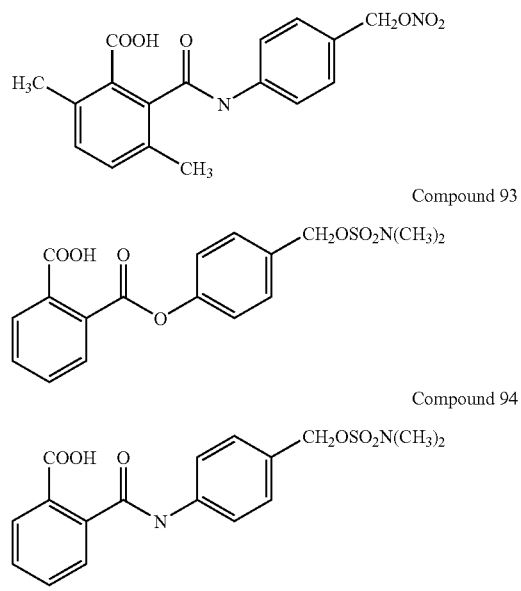

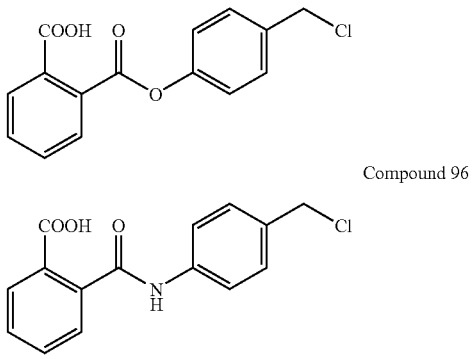

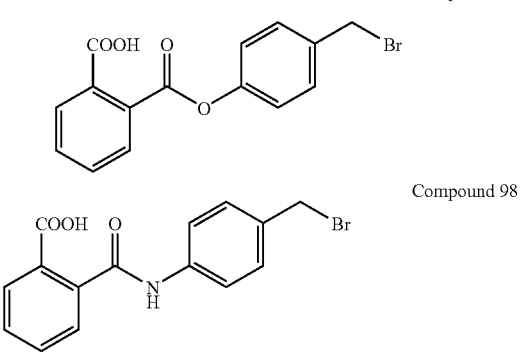

The foregoing compounds are merely illustrative of Formula I and are not intended to be limiting.

The invention embraces compounds of Formula I that are novel. As such, in one embodiment of the invention, compounds of Formula I exclude those wherein A is 2-acetyloxyphenyl, $X^1$ is —O—, $X^2$ is H and D is nitrate. Moreover, preferred compounds of Formula I of the invention include where A is 2-(3-fluoro-4-phenyl)phenyl-propionyl-, where $X^2$ is H; $X^1$ is —O—, and where D is —$ONO_2$, —Cl, or —Br.

It will be appreciated that for each of the classes and subclasses described above and herein, any one or more occurrences of aliphatic or heteroaliphatic may independently be substituted or unsubstituted, cyclic or acyclic, linear or branched and any one or more occurrences of aryl, heteroaryl, cycloaliphatic, cycloheteroaliphatic may be substituted or unsubstituted.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided. Moreover, when compounds of the invention exist in tautomeric forms, each tautomer is embraced herein.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (I) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them. Thus, compounds of the invention include their tautomers, prodrugs thereof, salts thereof, hydrates thereof and esters thereof.

In yet a further aspect, the invention is also directed to compounds and uses thereof that generate quinone methide or iminoquinone methide intermediates after the in vivo removal of certain moieties therefrom, such as substituent D and the substituent of Formula I comprising a portion of the substituent of Formula I comprising moiety A. As previously mentioned, and for theoretical purposes only and to which Applicant is not bound, hydrolysis of the ester or amide linking to moiety A (i.e., A-C(=O)O— or A-C(=O)NH—) and loss of leaving group D generate biologically active moieties that, among other actions, bind to and reduce the cellular level of compounds such as glutathione, which defend the cell against oxidative stress. Thus, the invention is also directed to such compounds, compositions comprising them, and methods of treating cancer and other dysproliferative diseases by administering to a patient or animal in need thereof, or to a site in said patient or animal's body, a quinone methide- or iminoquinone methide-generating compound of the invention. Such a compound may be considered a prodrug of a quinone methide or an iminoquinone methide. For example, compounds of the invention, for simplicity shown below wherein $R^2$=H, and where the D-$CH_2$— moiety is para or ortho to the A-C(=O)—$X^1$— moiety generate quinone methide or iminoquinone methide intermediates in vivo shown as follows:

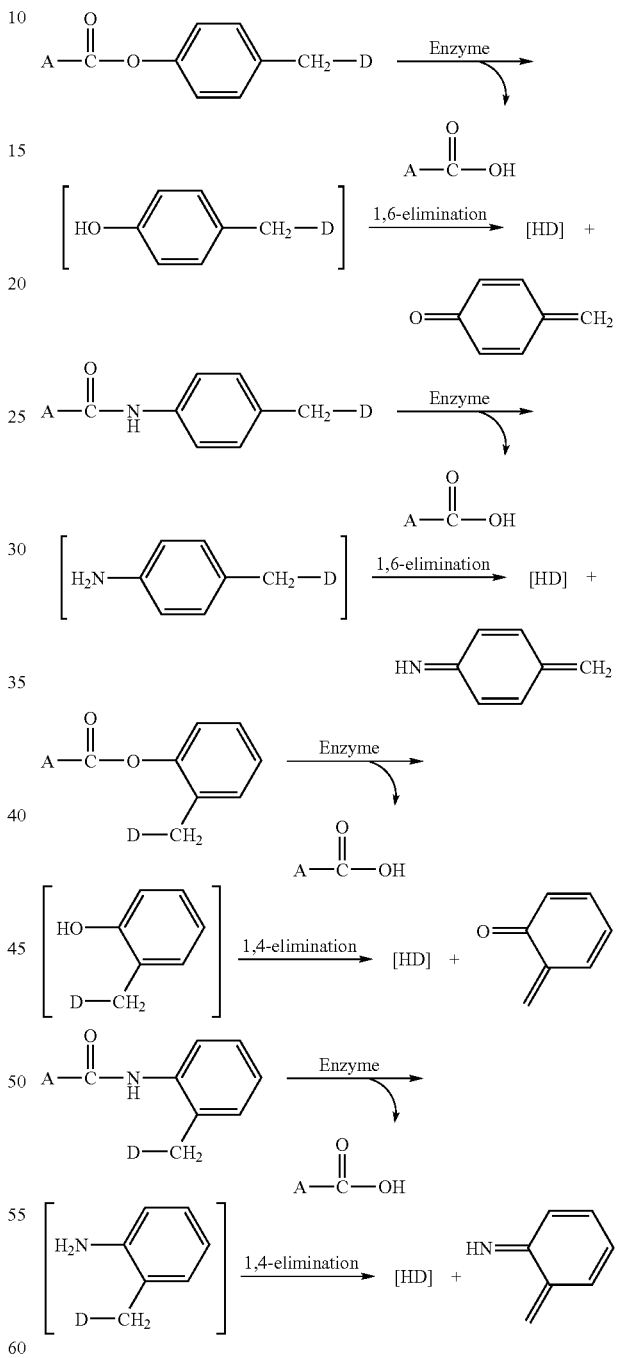

Compounds of the invention wherein the D-$CH_2$— moiety is meta to the A-C(=O)—$X^1$-moiety also generate moieties that kill cancer cells. Again, hydrolysis of the ester or amide linking to moiety A (i.e., A-C(=O)O— or A-C(=O)NH—) and loss of leaving group D generate biologically active moieties.

Thus, the invention is directed to the use of the aforementioned quinone methide- or iminoquinone methide-generating compounds for treating dysproliferative diseases such as cancer. While the para and ortho compounds are preferred, the invention is not limited thereto, and the meta compounds show biological activity via, but not limited to, the molecular remnant after removal of moieties A and D.

Thus, in a specific embodiment, the invention is directed to a method for obtaining a prodrug of a quinone methide or iminoquinone methide intermediate comprising formulating the compounds of the present invention into a composition comprising the compound of the present invention and a pharmaceutically acceptable carrier or excipient. The invention is further directed to uses of the compound of the present invention for manufacturing a medicament comprising a prodrug of a quinone methide or iminoquinone methide intermediate and a pharmaceutical composition comprising the composition of the present invention and a pharmaceutically acceptable carrier or excipient for use as a prodrug of a quinone methide or iminoquinone methide intermediate.

Compositions

As discussed above, this invention provides novel compounds that have biological properties useful for the treatment of any of a number of conditions or diseases generally characterized by abnormal cellular proliferation, or prophylaxis in instances wherein a risk of appearance of such conditions or diseases is present. Moreover, certain compounds known in the art have been newly identified as having activity likewise useful in the prophylaxis or treatment of abnormal cellular proliferation, and the invention is also directed to anti-cancer compositions comprising such compounds.

Accordingly, in another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved anti-cancer or anti-neoplastic agent, or it may be any one of a number of agents undergoing approval in the Food and Drug Administration that ultimately obtain approval for the treatment of any disorder related to neoplasia, cancer, or abnormal cellular proliferation in general. Such additional therapeutic agents may also be provided to promote the targeting of the compounds of the invention to the desired site of treatment, or may increase its stability, increase its half-life, etc. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T.

Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut (peanut), corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions to deliver the agent directly to the colon— for example, pills from which the active agent is released into the colon by a pH-dependent or other mechanism ensuring exclusive or predominant colonic delivery of said compound, suppositories, enemas and other means for colonic delivery.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include but are not limited to capsules, tablets, pills, powders, and granules. In such solid dosage forms, the active compound is mixed with at least one inert, pharmaceutically acceptable excipient or carrier such as sodium citrate or dicalcium phosphate and/ or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include but are not limited to polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, $16^{th}$ Edition, 1980 and $17^{th}$ Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerin, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel. It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-cancer agent), or they may achieve different effects (e.g., control of any adverse effects).

In certain embodiments, the pharmaceutical compositions of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

Uses and Methods of Treatment

According to the present invention, the inventive compounds may be assayed in any of the available assays known in the art for identifying compounds having the ability to modulate cell proliferation activity. For example, the assay may be cellular or non-cellular, in vivo or in vitro, high- or low-throughput format, etc.

As detailed in the exemplification herein, in assays to determine the ability of compounds to inhibit cell growth certain inventive compounds exhibited $IC_{50}$ values<1,000 µM. In certain other embodiments, inventive compounds exhibit $IC_{50}$ values≦500 µM. In certain other embodiments, inventive compounds exhibit $IC_{50}$ values≦100 µM. In certain other embodiments, inventive compounds exhibit $IC_{50}$≦50 µM. In certain other embodiments, inventive compounds exhibit $IC_{50}$ values≦40 µM. In certain other embodiments, inventive compounds exhibit $IC_{50}$ values≦30 µM. In certain other embodiments, inventive compounds exhibit $IC_{50}$ values≦20 µM. In certain other embodiments, inventive compounds exhibit $IC_{50}$ values≦10 µM. In certain other embodiments, inventive compounds exhibit $IC_{50}$ values≦7.5 µM. In certain embodiments, inventive compounds exhibit $IC_{50}$ values≦5 µM. In certain other embodiments, inventive compounds exhibit $IC_{50}$ values≦2.5 µM. In certain embodiments, inventive compounds exhibit $IC_{50}$ values≦1 µM. In certain other embodiments, inventive compounds exhibit $IC_{50}$ values≦750 nM. In certain other embodiments, inventive compounds exhibit $IC_{50}$ values≦500 nM. In certain other embodiments, inventive compounds exhibit $IC_{50}$ values≦250 nM. In certain other embodiments, inventive compounds exhibit $IC_{50}$ values≦100 nM. In other embodiments, exemplary compounds exhibited $IC_{50}$ values≦75 nM. In other embodiments, exemplary compounds exhibited $IC_{50}$ values≦50 nM. In other embodiments, exemplary compounds exhibited $IC_{50}$ values≦40 nM. In other embodiments, exemplary compounds exhibited $IC_{50}$ values≦30 nM. In other embodiments, exemplary compounds exhibited $IC_{50}$ values≦20 nM. In other embodiments, exemplary compounds exhibited $IC_{50}$ values≦10 nM. In other embodiments, exemplary compounds exhibited $IC_{50}$ values≦5 nM.

As discussed above, certain of the compounds as described herein exhibit activity generally as modulators of cell growth, defined as the net result of cell renewal and cell death. In this formulation, proliferation is understood as cell renewal, while cell death is understood as either apoptosis or cell necrosis. More specifically, compounds of the invention demonstrate the ability to reduce or inhibit the growth of cells through a combined action on cell proliferation (inhibition) and cell death (induction) where such growth of cells in the body is considered abnormal and/or detrimental to the health and well being of the individual. Such abnormal cellular growth characterizes any one of many of so-called dysproliferative diseases including neoplasia and cancer, malignant and benign tumor growth, and other conditions such as but not limited to psoriasis. Thus, in certain embodiments, compounds of the invention are useful for the treatment of any of a number of conditions or diseases in which or the activities thereof have a therapeutically useful role.

Accordingly, in another aspect of the invention, methods for the treatment of abnormal cell growth-related disorders are provided comprising administering a therapeutically effective amount of a compound of formula (I) as described herein, to a subject in need thereof. In certain embodiments, a method for the treatment of related disorders is provided comprising administering a therapeutically effective amount of an inventive compound, or a pharmaceutical composition comprising an inventive compound to a subject in need thereof, in such amounts and for such time as is necessary to achieve the desired result.

The invention is also directed to the use of any compound of Formula (I) for the preparation of a medicament for administration to a human or animal patient in need thereof, to treat cancer, inhibit or block the growth of dysproliferative cells, or prevent the development of neoplastic diseases or the development of preneoplastic entities such as, for example but not limited to the aberrant crypt foci in the colon. Such compounds preferably are administered once a dysproliferative disease has been diagnosed in the patient, optionally in combination with other anti-cancer agents or other agents such as those that maintain therapeutic levels of the compounds within the body. Compounds of the invention also may be administered after other therapies have been tried and failed, and may be administered prophylactically particularly in patients predisposed to develop dysproliferative disease.

In certain embodiments, the uses and methods of the invention involve the administration of a therapeutically effective amount of the compound or a pharmaceutically acceptable derivative thereof to a subject (including, but not limited to a human or animal, including livestock, domesticated or zoo animals) in need thereof.

As discussed above, this invention provides compounds that have biological properties useful for the treatment of any human and animal neoplastic conditions, both benign and malignant and conditions that have as one of its features increased cell proliferation or diminished cell death, such as but not limited to psoriasis, which are not considered as neoplastic per se; conditions like actinic keratosis; and other similar conditions to name a few. In certain embodiments of special interest, the inventive method is used for the treatment of cancers of the colon, pancreas, prostate, lung, breast, urinary bladder, skin and liver (both primary such as hepatoma and metastatic from other primary sites, such as but not limited to the colon or the lung, as well as benign liver tumors). Examples of other cancers, tumors, malignancies, neoplasms, and other dysproliferative diseases that can be treated according to the invention include leukemias such as myeloid and lymphocytic leukemias, lymphomas, myeloproliferative diseases, and solid tumors, such as but not limited to sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, carcinoma of the tongue, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. These diseases are merely exemplary of a variety of dysproliferative diseases amenable to treatment by compounds described herein.

It will be appreciated that the compounds and compositions, according to the method of the present invention, may be administered using any amount and any route of administration effective for the treatment of conditions or diseases in which anticancer or related activities have a therapeutically useful role. Thus, the expression "effective amount" as used herein, refers to a sufficient amount of agent to inhibit cellular proliferation and to exhibit a therapeutic effect. The exact amount required will vary from subject to subject, depending on the species, age, and general condition of the subject, the severity of the infection, the particular therapeutic agent, its mode of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the location and extent of the dysproliferative disease being treated. In certain embodiments, the compounds of the invention may be parenterally administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. In other embodiments, compounds of the invention may be administered orally or rectally at dosage levels of about 0.01 mg/kg to about 100 mg/kg, from about 0.05 mg/kg to about 50 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

General Description of Synthetic Methods:

The following reaction scheme was followed to obtain compounds (F) and (G) of the invention described herein below:

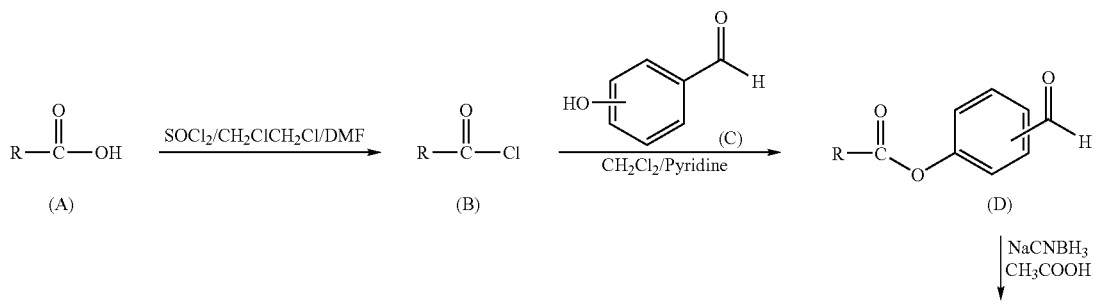

-continued

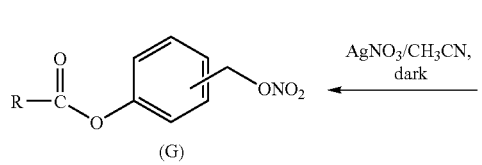 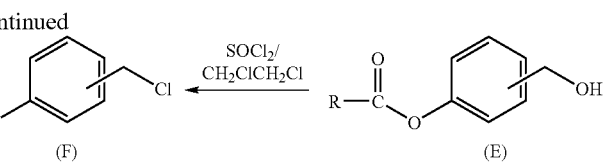

The starting compound A is an aliphatic or an aromatic carboxylic acid, which it may or may not be substituted. This is reacted with thionyl chloride in order to produce the acid chloride, compound B. In essence compound A is made more reactive by this conversion. Compound B is then coupled with para-, or ortho-, or meta-hydroxy benzaldehyde (compound C) to produce compound D. This is then reduced to compound E, which is an alcohol. Compound E is then made more reactive by converting it to its corresponding chloride, compound F, which is then nitrated to give compound G. Replacing thionyl chloride with thionyl bromide in the reaction (E) to (F) above generates the corresponding bromide.

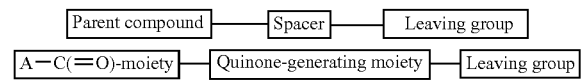

The parent compound should be electron donating and may be an A-C=O moiety, the leaving group must be a good leaving group, so that the spacer, a quinone generating moiety, can be activated to the quinone methide. If the starting material is a para-, or ortho-, or meta-aminobenzaldehyde an iminoquinone methide may be obtained.

The practitioner has a well-established literature of small molecule chemistry to draw upon, in combination with the information contained herein, for guidance on synthetic strategies, protecting groups, and other materials and methods useful for the synthesis of the compounds of this invention. The various references cited herein provide helpful background information on preparing compounds similar to the inventive compounds described herein or relevant intermediates, as well as information on formulation, uses, and administration of such compounds which may be of interest. Moreover, the practitioner is directed to the specific guidance and examples provided in this document relating to various exemplary compounds and intermediates thereof. Variations of the invention, now known or further developed, are considered to fall within the scope of the present invention as described herein and as hereinafter claimed.

The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5$^{th}$ ed. John Wiley and Sons, New York, N.Y.; and Larock 1990, "Comprehensive Organic Transformations: A Guide to Functional Group Preparations", 2$^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

General Reaction Procedures

Unless mentioned specifically, reaction mixtures were stirred using a magnetically driven stirrer bar. An inert atmosphere refers to either dry argon or dry nitrogen. Reactions were monitored either by thin layer chromatography, by proton nuclear magnetic resonance ($^1$H NMR) or by high-pressure liquid chromatography (HPLC), of a suitably worked up sample of the reaction mixture.

General Work Up Procedures

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, and then filtered. The crude products were then isolated by removal of solvent(s) by rotary evaporation under reduced pressure, at an appropriate temperature (generally less than 45° C.).

General Purification Procedures

Unless mentioned specifically, chromatographic purification refers to flash column chromatography on silica, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

Analyses

To confirm purity and identity of the compounds of the invention, TLC, and $^1$H NMR were performed.

EXAMPLES

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

Synthesis of Exemplary Compounds

Unless otherwise indicated, starting materials are either commercially available or readily accessibly through laboratory synthesis by anyone reasonably familiar with the art. Described generally below, are procedures and general guidance for the synthesis of compounds as described generally and in subclasses and species herein.

1. Synthesis of Flurbiprophen Derivatives

The following reaction scheme was followed to obtain compounds (F) and (G) of the invention: 4-O-[2-(3-fluoro-4-phenyl)phenyl propionyl]-4-hydroxybenzyl chloride (F) and 4-O-[2(3-fluoro-4-phenyl)phenyl propionyl]-4-hydroxybenzyl nitrate (G).

Flurbiprophen (Compound A, 50 g, 204 mmol) was heated overnight under reflux with $SOCl_2$ (44.8 mL, 614 mmol) in 1,2-dichloroethane (300 mL) and DMF (1 mL) to obtain Compound B (yield was quantitative). Compound B was reacted with p-hydroxy benzaldehyde (Compound C, 24.27 g, 199 mmol) in $CH_2Cl_2$ (400 mL) and pyridine (49 mL) to obtain Compound D (yield was quantitative). Compound D was reduced using NaCNBH3 in acetic acid to obtain compound E (yield was quantitative). Compound E (43 g, 123 mmol) was heated over night under reflux with $SOCl_2$ (44.8 mL, 614 mmol) in 1,2-dichloroethane (300 mL) and DMF (1 mL) to obtain Compound F (yield was quantitative). In a separate preparation, compound F was isolated and tested as a final product. In another preparation, Compound F was refluxed for 3 hr in the dark with silver nitrate (187 mmol) in acetonitrile (350 mL) to obtain the final product, Compound G.

Compounds F and G were purified by silica gel chromatography and crystallized from ethyl acetate/n-hexane (yield was 39.5 g, 81%). Purity of compound G was >98% by TLC

Figure 3:
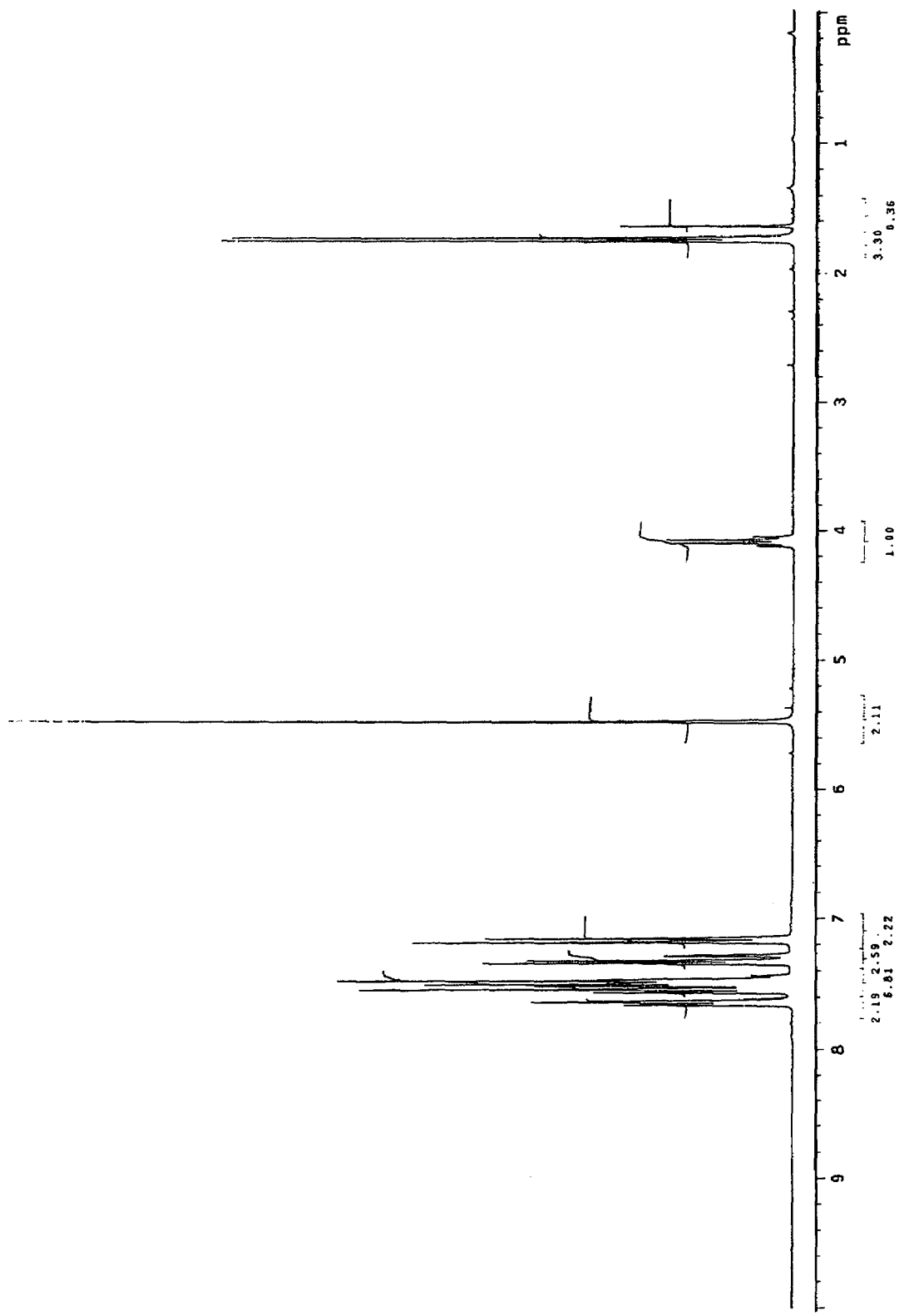
FIG. 3 shows an NMR spectrum of 4-O-[2-(3-fluoro-4-phenyl)phenyl propionyl]-4-hydroxybenzyl nitrate (Compound 5).
Figure 4:
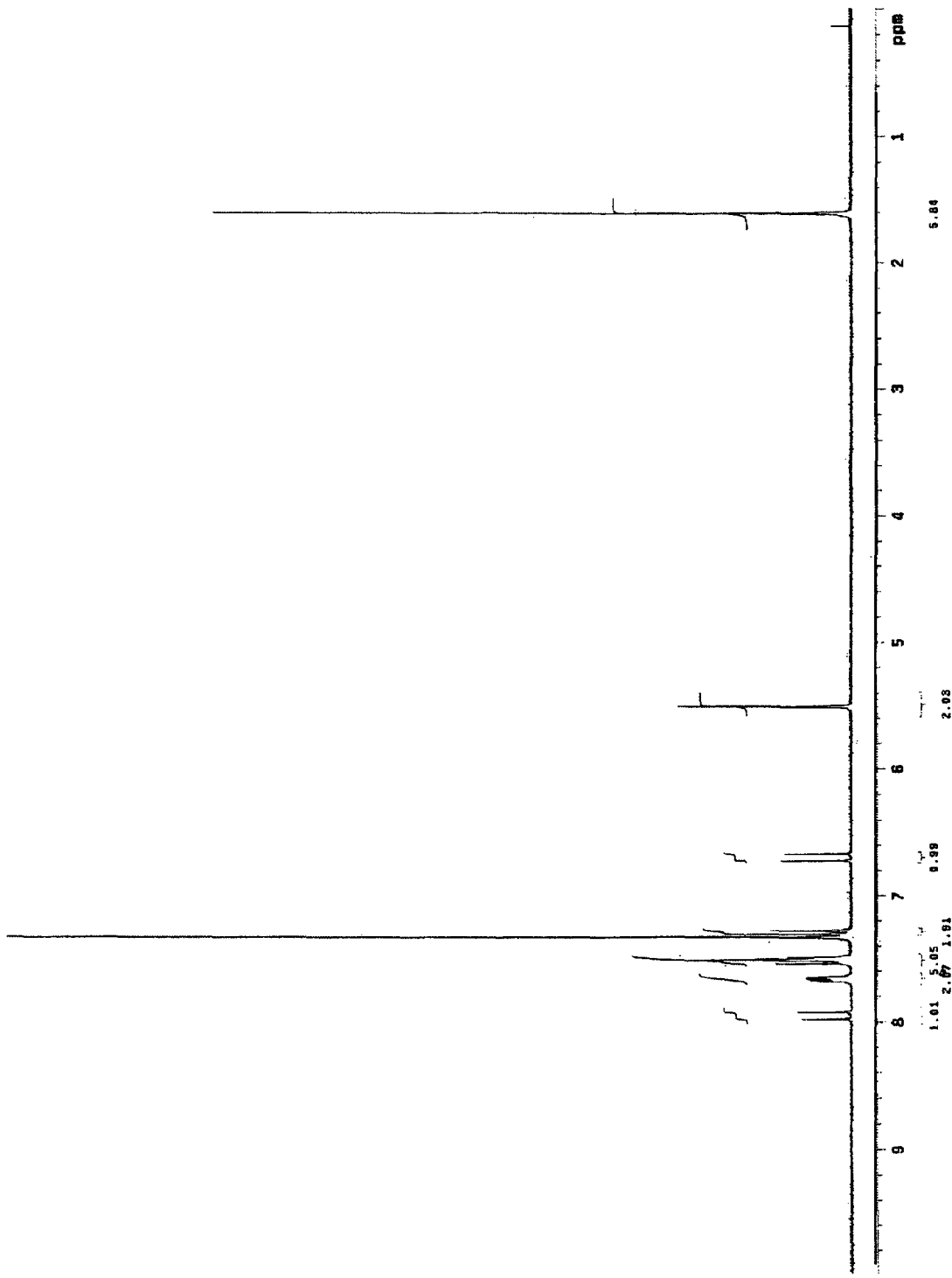
FIG. 4 shows an NMR spectrum of cinnamic acid 4-(nitrooxymethyl)phenyl ester (Compound 63).
Figure 5:
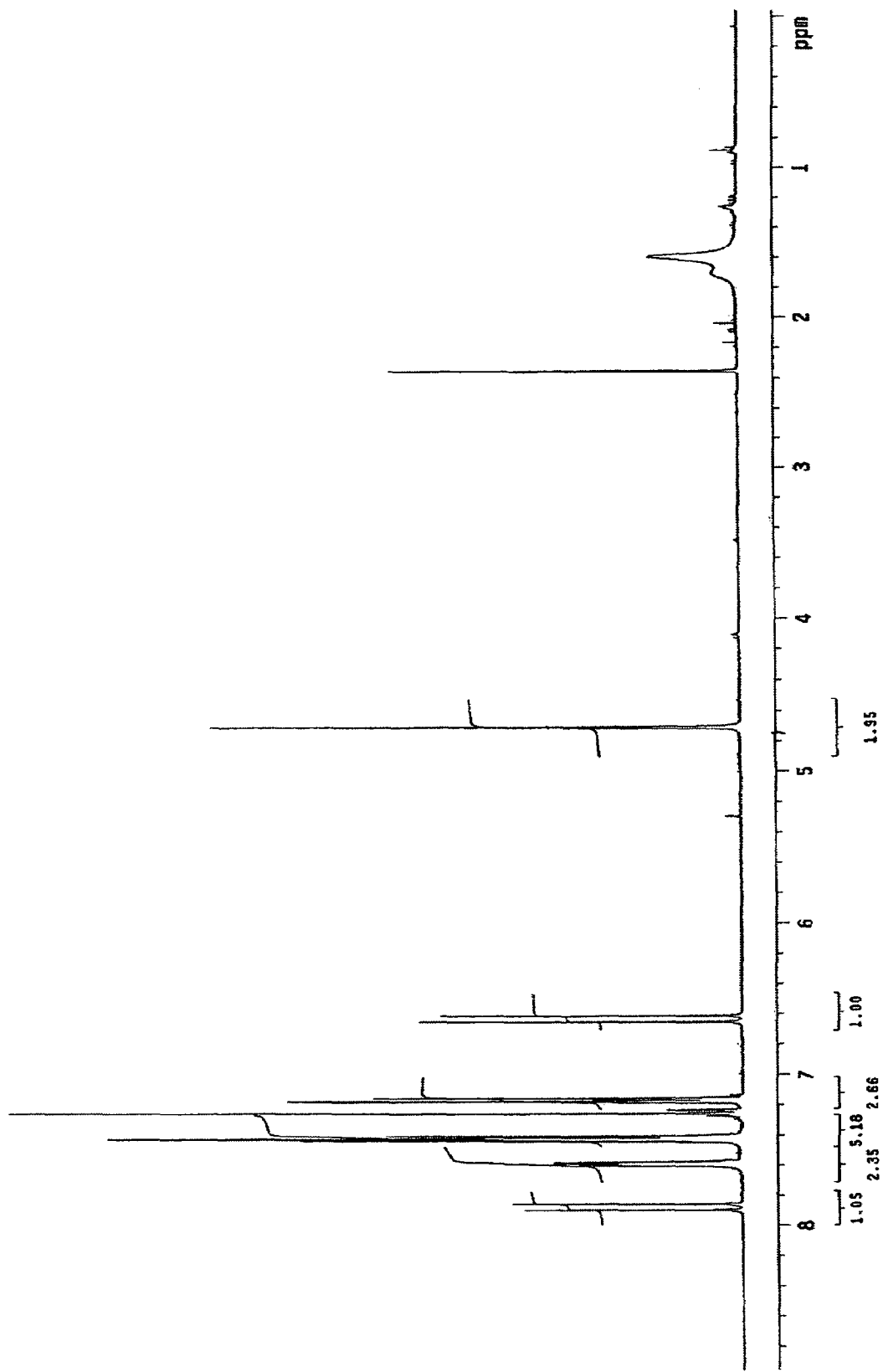
FIG. 5 shows an NMR spectrum of cinnamic acid 4-(hydroxymethyl)phenyl ester.
Figure 6:
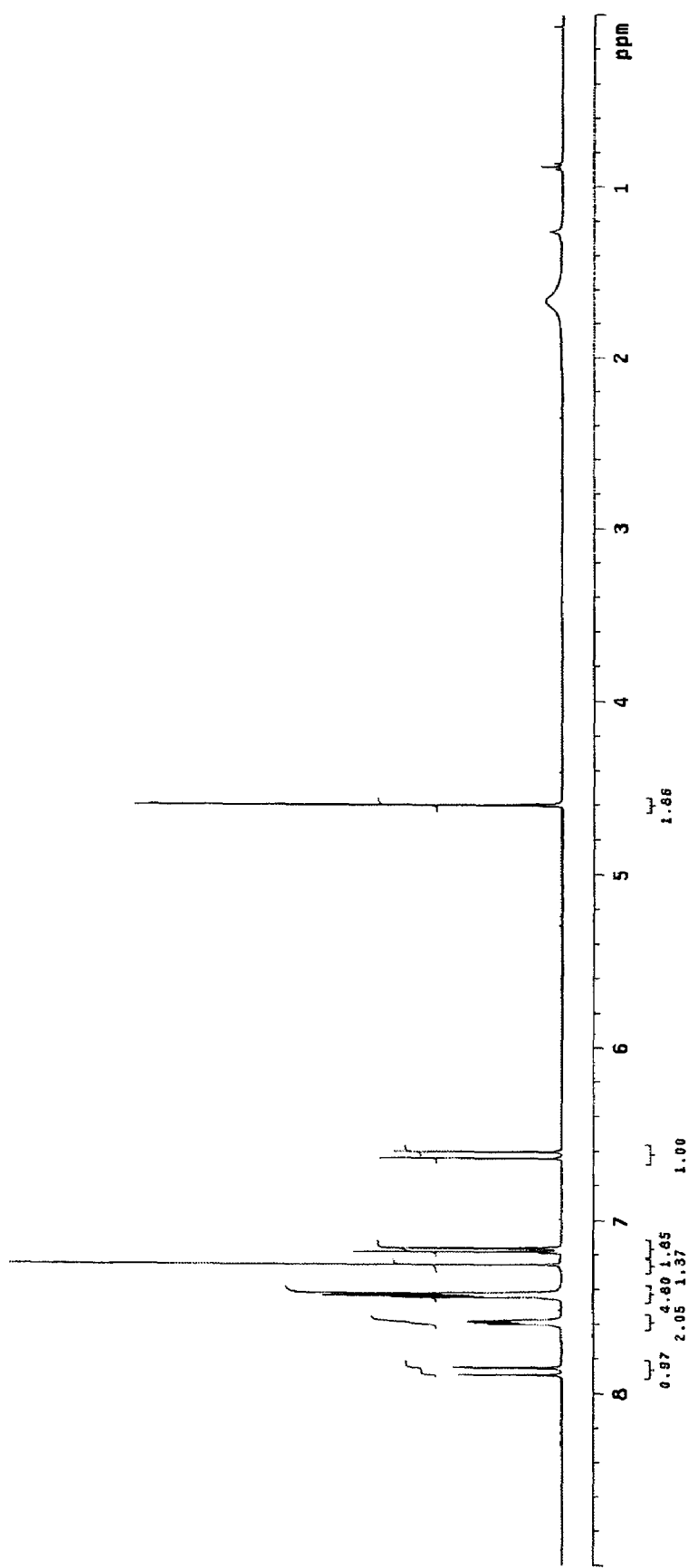
FIG. 6 shows an NMR spectrum of cinnamic acid 4-(chloromethyl)phenyl ester (Compound 69).

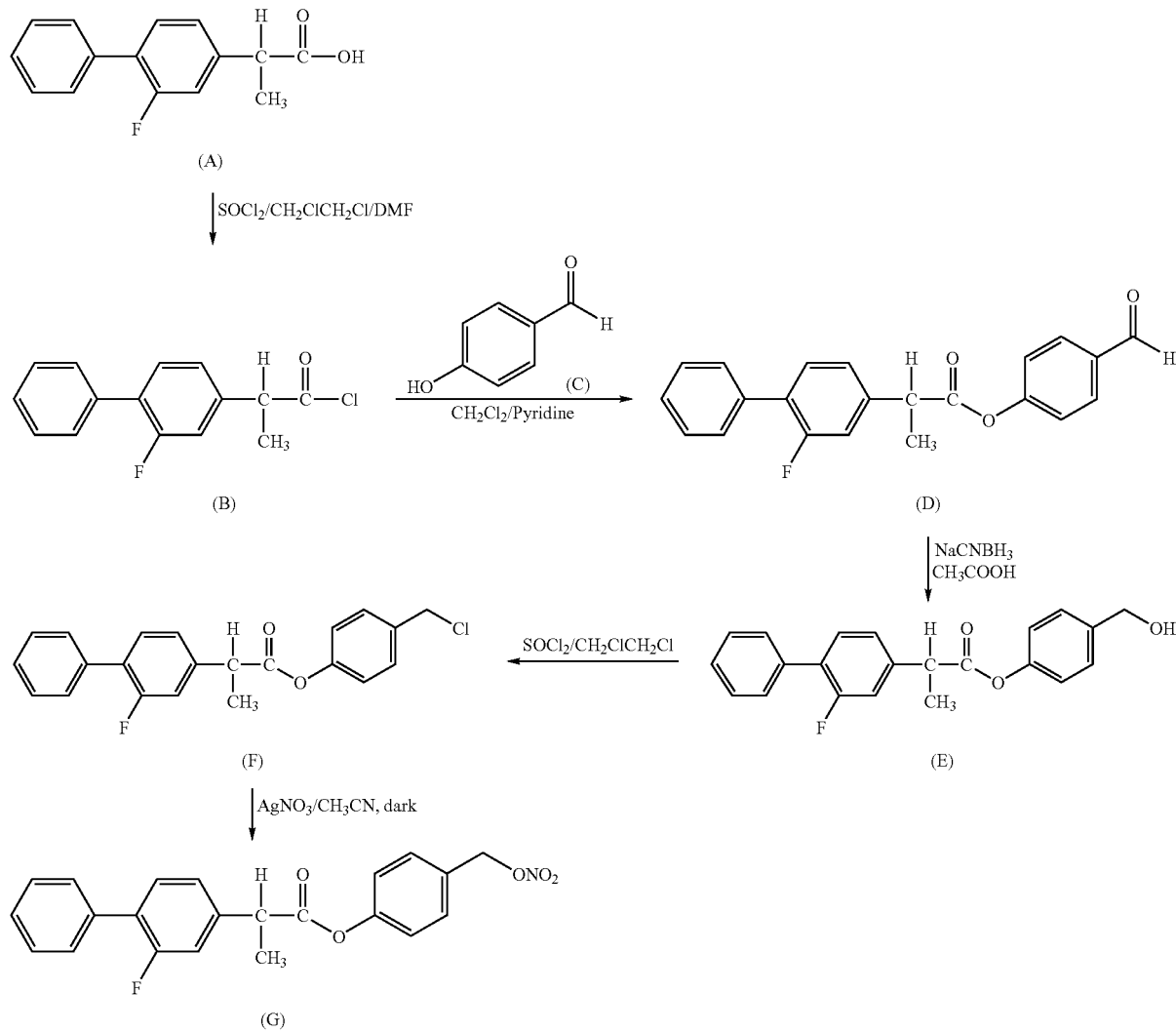

and 1H NMR (FIG. 3). Compounds F and G correspond to Compounds 9 and 5 described above, respectively.

2. Synthesis of Cinnamic Acid Derivatives

The diagram below outlines the synthesis of 4-O-(3,4-dimethoxy cinnamoyl)-4-hydroxyphenyl-methyl nitrate.

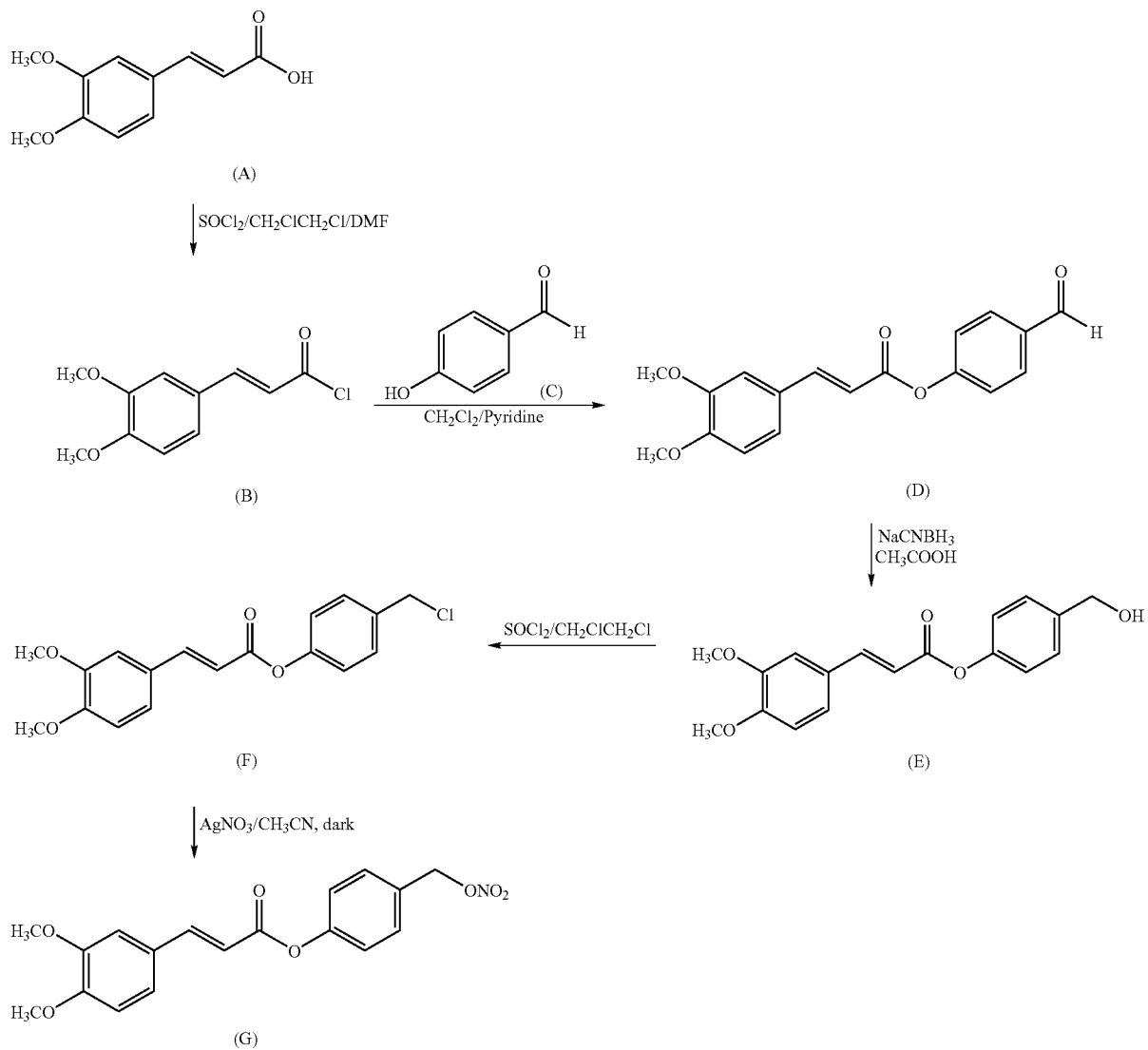

Figure 7:
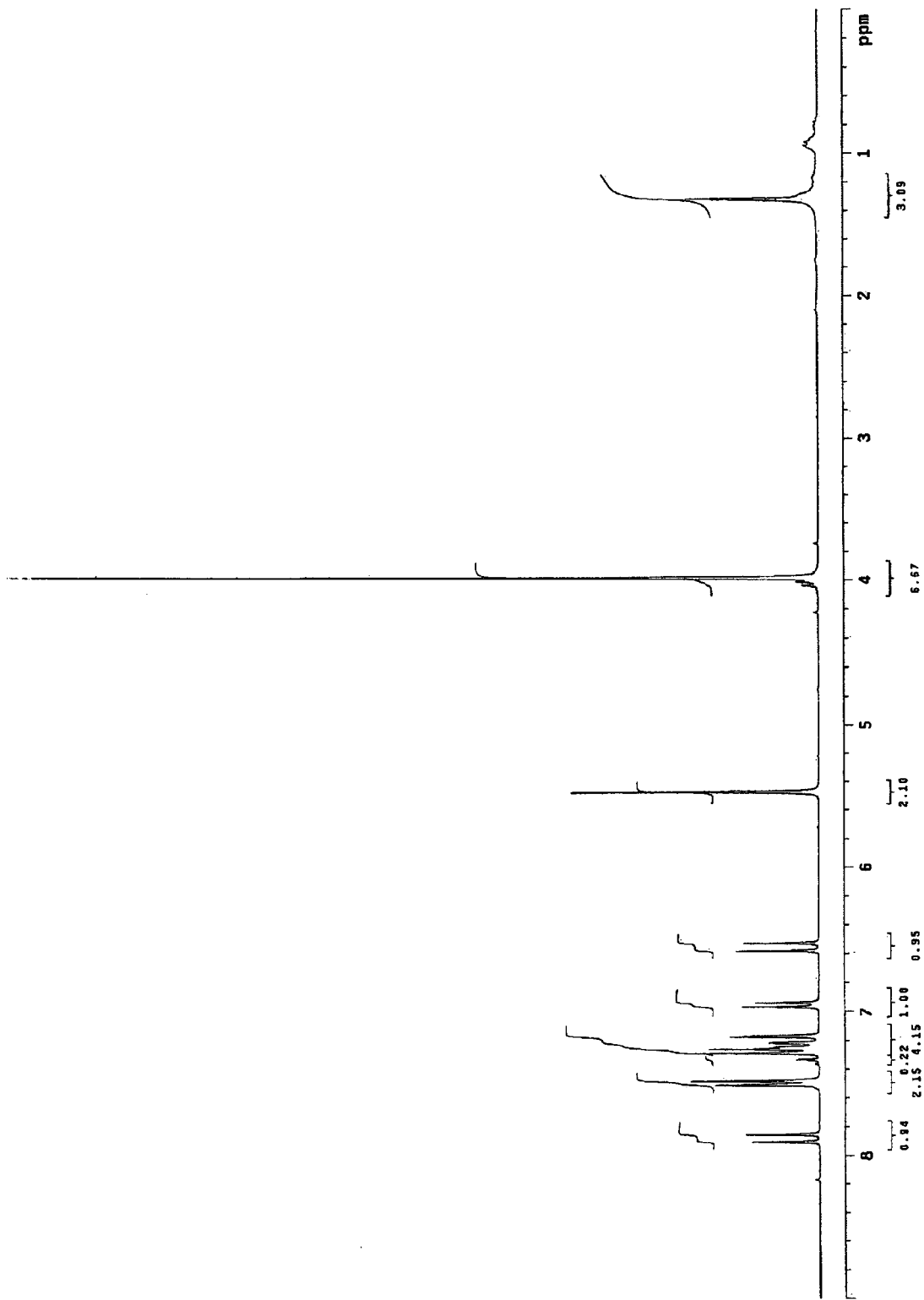
FIG. 7 shows an NMR spectrum of 3,4-dimethoxycinnamic acid 4-(nitrooxy methyl)phenyl ester (Compound 81).

Using this approach the end-product (G) was obtained with a purity of >98% by TLC and 1H NMR (FIG. 7). Compounds (E) and (F) were also obtained as end products and evaluated. The following compounds were prepared using the methods described above: Compounds 1-2, 6-8, 12-14, and 18-20;

Following the same procedures described above, the following cinnamic acid analogs are used to make the corresponding compounds of the invention:
cinnamic acid
4-nitro-alpha-(ortho-tolyl)cinnamic acid;
3-(trifluoromethyl)cinnamic acid;
alpha-(bromomethyl)cinnamic acid;
trans-2,5-bis(trifluoromethyl)cinnamic acid;
trans-3,5-bis((trifluoromethyl)cinnamic acid;
trans-2,6-dichloro-cinnamic acid;
2-bromo-4,5-(dimethoxy)cinnamic acid;
2-(hexadecyloxy)cinnamic acid;
2-(trifluoromethyl)cinnamic acid;
3-(trifluoromethoxy)cinnamic acid;
3,4-dimethoxycinnamic acid; and
4-(anisylideneamino)-cinnamic acid Flurbiprophen Derivatives:
4-O-[2-(3-fluoro-4-phenyl)phenyl propionyl]-3-hydroxybenzyl nitrate (Compound 3).
4-O-[2-(3-fluoro-4-phenyl)phenyl propionyl]-2-hydroxybenzyl nitrate (Compound 4).
4-O-[2-(3-fluoro-4-phenyl)phenyl propionyl]-4-hydroxybenzyl nitrate (Compound 5).
4-O-[2-(3-fluoro-4-phenyl)phenyl propionyl]-3-hydroxybenzyl chloride (Compound 9)
4-O-[2-(3-fluoro-4-phenyl)phenyl propionyl]-2-hydroxybenzyl chloride (Compound 10)
4-O-[2-(3-fluoro-4-phenyl)phenyl propionyl]-4-hydroxybenzyl chloride (Compound 11)

4-O-[2-(3-fluoro-4-phenyl)phenyl propionyl]-3-hydroxybenzyl bromide (Compound 15)
4-O-[2-(3-fluoro-4-phenyl)phenyl propionyl]-2-hydroxybenzyl bromide (Compound 16)
4-O-[2-(3-fluoro-4-phenyl)phenyl propionyl]-4-hydroxybenzyl bromide (Compound 17)

Aspirin Derivatives:
2-(acetyloxy)benzoic acid 3-(nitromethyl)phenyl amide (Compound 21)
2-(acetyloxy)benzoic acid 2-(nitromethyl)phenyl amide (Compound 22)
2-(acetyloxy)benzoic acid 4-(nitromethyl)phenyl amide (Compound 23)
2-(acetyloxy)benzoic acid 3-(chloromethyl)phenyl amide (Compound 24)
2-(acetyloxy)benzoic acid 2-(chloromethyl)phenyl amide (Compound 25)
2-(acetyloxy)benzoic acid 4-(chloromethyl)phenyl amide (Compound 26)
2-(acetyloxy)benzoic acid 3-(bromomethyl)phenyl amide (Compound 27)
2-(acetyloxy)benzoic acid 2-(bromomethyl)phenyl amide (Compound 28)
2-(acetyloxy)benzoic acid 4-(bromomethyl)phenyl amide (Compound 29)
2-(acetyloxy)benzoic acid 3-(sulfonamidoxymethyl)phenyl ester (Compound 30)
2-(acetyloxy)benzoic acid 2-(sulfonamidoxymethyl)phenyl ester (Compound 31)
2-(acetyloxy)benzoic acid 4-(sulfonamidoxymethyl)phenyl ester (Compound 32)
2-(acetyloxy)benzoic acid 3-(chloromethyl)phenyl ester (Compound 33)
2-(acetyloxy)benzoic acid 2-(chloromethyl)phenyl ester (Compound 34)
2-(acetyloxy)benzoic acid 4-(chloromethyl)phenyl ester (Compound 35)
2-(acetyloxy)benzoic acid 3-(bromomethyl)phenyl ester (Compound 36)
2-(acetyloxy)benzoic acid 2-(bromomethyl)phenyl ester (Compound 37)
2-(acetyloxy)benzoic acid 4-(bromomethyl)phenyl ester (Compound 38)

Caffeic Acid Derivatives:
caffeic acid 3-(nitrooxy methyl)phenyl ester (Compound 39)
caffeic acid 2-(nitrooxy methyl)phenyl ester (Compound 40)
caffeic acid 4-(nitrooxy methyl)phenyl ester (Compound 41)
caffeic acid 3-(nitrooxy methyl)phenyl amide (Compound 42)
caffeic acid 2-(nitrooxy methyl)phenyl amide (Compound 43)
caffeic acid 4-(nitrooxy methyl)phenyl amide (Compound 44)
caffeic acid 3-(chloro methyl)phenyl ester (Compound 45)
caffeic acid 2-(chloro methyl)phenyl ester (Compound 46)
caffeic acid 4-(chloro methyl)phenyl ester (Compound 47)
caffeic acid 3-(chloro methyl)phenyl amide (Compound 48)
caffeic acid 2-(chloro methyl)phenyl amide (Compound 49)
caffeic acid 4-(chloro methyl)phenyl amide (Compound 50)
caffeic acid 3-(bromo methyl)phenyl ester (Compound 51)
caffeic acid 2-(bromo methyl)phenyl ester (Compound 52)
caffeic acid 4-(bromo methyl)phenyl ester (Compound 53)
caffeic acid 3-(bromo methyl)phenyl amide (Compound 54)
caffeic acid 2-(bromo methyl)phenyl amide (Compound 55)
caffeic acid 4-(bromo methyl)phenyl amide (Compound 56)
3,5-dihydroxycinnamic acid 4-(nitrooxy methyl)phenyl ester (Compound 57)
3,5-dihydroxycinnamic acid 4-(nitrooxy methyl)phenyl amide (Compound 58)
3-hydroxy, 4-methoxycinnamic acid 4-(nitrooxy methyl)phenyl ester (Compound 59)
3-hydroxy, 4-methoxycinnamic acid 4-(nitrooxy methyl)phenyl amide (Compound 60)

Cinnamic Acid Derivatives:
cinnamic acid 3-(nitrooxy methyl)phenyl ester (compound 61)
cinnamic acid 2-(nitrooxy methyl)phenyl ester (compound 62)
cinnamic acid 4-(nitrooxy methyl)phenyl ester (compound 63)
cinnamic acid 3-(nitrooxy methyl)phenyl amide (compound 64)
cinnamic acid 2-(nitrooxy methyl)phenyl amide (compound 65)
cinnamic acid 4-(nitrooxy methyl)phenyl amide (compound 66)
cinnamic acid 3-(chloro methyl)phenyl ester (compound 67)
cinnamic acid 2-(chloro methyl)phenyl ester (compound 68)
cinnamic acid 4-(chloro methyl)phenyl ester (compound 69)
cinnamic acid 3-(chloro methyl)phenyl amide (compound 70)
cinnamic acid 2-(chloro methyl)phenyl amide (compound 71)
cinnamic acid 4-(chloro methyl)phenyl amide (compound 72)
cinnamic acid 3-(bromo methyl)phenyl ester (compound 73)
cinnamic acid 2-(bromo methyl)phenyl ester (compound 74)
cinnamic acid 4-(bromo methyl)phenyl ester (compound 75)
cinnamic acid 3-(bromo methyl)phenyl amide (compound 76)
cinnamic acid 2-(bromo methyl)phenyl amide (compound 77)
cinnamic acid 4-(bromo methyl)phenyl amide (compound 78)
3,4-dimethoxycinnamic acid 3-(nitrooxy methyl)phenyl ester (compound 79)
3,4-dimethoxycinnamic acid 2-(nitrooxy methyl)phenyl ester (compound 80)
3,4-dimethoxycinnamic acid 4-(nitrooxy methyl)phenyl ester (compound 81)
3,4-dimethoxycinnamic acid 3-(nitrooxy methyl)phenyl amide (compound 82)
3,4-dimethoxycinnamic acid 2-(nitrooxy methyl)phenyl amide (compound 83)
3,4-dimethoxycinnamic acid 4-(nitrooxy methyl)phenyl amide (compound 84)

Resveratrol Derivatives:
acetic acid (4-nitroxymethyl)phenyl-3-acyl-(3,5-dimethoxy)resveratrol (Compound 85)
acetic acid (4-methylsufonamide)phenyl-3-acyl-(3,5-dimethoxy)resveratrol (Compound 86)
acetamide (4-nitroxymethyl)phenyl-3-acyl-(3,5-dimethoxy)resveratrol (Compound 87)
acetamide (4-methylsufonamide)phenyl-3-acyl-(3,5-dimethoxy)resveratrol (Compound 88)

Phtahlic Acid Derivatives
phthalic acid 4-(nitrooxy methyl)phenyl ester (Compound 89)
phthalic acid 4-(nitrooxy methyl)phenyl amide (Compound 90)
2,4-dimethylphthalic acid 4-(nitrooxy methyl)phenyl ester (Compound 91)
2,4-dimethylphthalic acid 4-(nitrooxy methyl)phenyl amide (Compound 92)
phthalic acid 4-(dimethylsulfonamidoxymethyl)phenyl ester (Compound 93)
phthalic acid 4-(dimethlylsulfonamidoxymethyl)phenyl amide (Compound 94)

phthalic acid 4-(chloromethyl)phenyl ester (Compound 95)
phthalic acid 4-(chloro methyl)phenyl amide (Compound 96)
phthalic acid 4-(bromomethyl)phenyl ester (Compound 97)
phthalic acid 4-(bromomethyl)phenyl amide (Compound 98)

Evaluation of Antineoplastic Activity

Reagents: Stock (100 mM) solutions of all test reagents were prepared in dimethylsulfoxide (DMSO; from Fisher Scientific, Fair Lawn, N.J.). All compounds were added to the culture medium either immediately prior to plating cells or 16-24 hours after plating of cells to ensure their attachment to the culture dish. Final DMSO concentration was adjusted in all media to 1%. Exposure to the test drug varied, being usually between 24 and 72 hours.

Cell lines: HT-29 or HCT-15 human colon adenocarcinoma and other human cancer cell lines such as: SSC-25, squamous cell carcinoma of the tongue; A549, carcinoma of the lung; LNCaP, carcinoma of the prostate, MIA-Paca2 and BxPC3, carcinoma of pancreas; MCF-7, carcinoma of the breast; and A-431, carcinoma of the skin (American Type Tissue Collection, Rockville, Md.) were grown as monolayers in McCoy 5A, RPMI or other culture medium, respectively, as appropriate, supplemented with 10% fetal calf serum (Mediatech, Herndon, Va.), penicillin (50 μ/ml) and streptomycin (50 μ/ml) (GIBCO, Grand Island, N.Y.). In some experiments, cells were seeded at a density of $1.5 \times 10^6$ cells per 100-cm² culture dish and incubated at 37° C. in 5% CO2 and 90% relative humidity. Single cell suspensions were obtained by trypsinization (0.05% trypsin/EDTA) and cells were counted using a hemacytometer. Viability was determined by the trypan blue dye exclusion method.

Studies following the approach described above using flurbiprophen derivatives of the invention, as those described herein have provided the following results, indicating that these compounds are highly effective in inhibiting the growth of animal and human neoplastic cells, including malignant cells.

HT-29 human colon cells were plated at $0.25 \times 10^6$ per well of about 3 cm in diameter and about 16 hours later were exposed to Compound 1 at concentrations of 25, 50, 100, 200 and 500 micromolar. At 48 hrs the number of cells, expressed as percentage of the number of cells of untreated control samples, were 75%, 57%, 45% and 43%, and 37%, respectively, providing for an IC50 of about 73 micromolar. These values are the average of duplicates that did not differ by more than 9%.

The following table sets forth in vitro IC50 (in μM) data on inventive compound 4-O-[2-(3-fluoro-4-phenyl)phenyl propionyl]-4-hydroxybenzyl nitrate (compound 5), using the indicated cancer cell lines and following the experimental protocol outlined above, allowing for variations in the concentration of the test compounds, depending on their potency and the cell line which was exposed to each one of them.

The IC50 (expressed in μM) at 24 hr was also determined in colon cancer HT-29 and pancreatic cancer BxPC3 for other inventive compounds.

| Compound | HT-29, colon | BxPC3, pancreas |
| --- | --- | --- |
| Aspirin | >1000 | >1000 |
| 2-(acetyloxy)-4-[(nitrooxy)methyl] phenyl ester (compound 23) | 25 ± 4 | ND |
| 2-(acetyloxy)benzoic acid 4-(bromomethyl)phenyl ester (Compound 29) | 7 ± 2 | 18 ± 3 |
| 2-(acetyloxy)benzoic acid 4-(chloromethyl)phenyl ester (Compound 26) | 12 ± 3 | ND |
| 2-(acetyloxy)benzoic acid 4-(hydroxymethyl)phenyl ester | >500 | >500 |
| Caffeic acid | >1000 | >1000 |
| Caffeic acid 4-(nitrooxy methyl)phenyl ester (compound 41) | ~0.5 | ND |
| Caffeic acid 4-(hydroxy methyl)phenyl ester | >500 | ND |
| Caffeic acid 4-(chloro methyl)phenyl ester (compound 47) | 0.25 | ND |
| Cinnamic acid 4-(hydroxy methyl)phenyl ester | 150 ± 12 | ND |
| Cinnamic acid 4-(chloro methyl)phenyl ester (compound 69) | 6 ± 1 | 4 ± 1 |
| 3,4-dimethoxycinnamic acid 4-(nitrooxy methyl)phenyl ester (Compound 81) | 33 ± 4 | 18 ± 3 |

ND = Not determined

The Colony Formation Assay, also known as "soft agar assay for colony formation" as described by David Bowtell (accessed on the Internet as recently as on Dec. 29, 2003 at http://grimwade.biochem.unimelb.edu.au/bowtell/cellbiol/sect71.htm) was also used to asses the neoplastic cell growth inhibitory effect of these compounds and using the JB6c141 rat skin cells. Briefly, and following the plating of cells in the presence or absence of epidermal growth factor and in each case, in the presence or absence of the test compound, they were incubated at 370 C in a humidified incubator for 14 days, when plates were stained 0.005% Crystal Violet for >1 hour, colonies were counted using a dissecting microscope.

The results of this experiment revealed that treatment of these cells by Compound 1 at a concentration of 100 micromolar abolished colony formation; untreated cells formed between 24 and 86 colonies depending on the absence or presence of epidermal growth factor, respectively.

In vivo Data using 4-O-[2-(3-fluoro-4-phenyl)phenyl propionyl]-4-hydroxybenzyl nitrate (Compound 5)

The ability of 4-O-[2-(3-fluoro-4-phenyl)phenyl propionyl]-4-hydroxybenzyl nitrate to inhibit the development of

| | Tumor origin and cell line | | | | | | | |
| --- | --- | --- | --- | --- | --- | --- | --- | --- |
| | Colon | | Skin | Breast | Tongue | Lung | Prostate | Pancreas |
| Time | HT-29 | HCT-15 | A-431 | MCF-7 | SSC-25 | A549 | Lncap | MIA Paca2 | BxPC3 |
| 24 hr | 49 ± 4 | 62 ± 3 | 48 ± 5 | 77 ± 8 | 8 ± 3 | 65 ± 4 | 35 ± 4 | 72 ± 3 | 25 ± 3 |
| 48 hr | 41 ± 2 | 35 ± 4 | 40 ± 3 | 59 ± 5 | 6 ± 2 | 58 ± 3 | 15 ± 3 | 65 ± 2 | 20 ± 2 |
| 72 hr | 28 ± 4 | 15 ± 6 | 29 ± 4 | ND | ND | ND | ND | ND | ND |

ND = Not determined gastrointestinal tumors in the Min (Apcmin/+) mouse model of intestinal cancer was evaluated. Min mice have a truncating mutation in the Apc gene that predisposes them to the development of gastrointestinal tumors, mainly in the small intestine (Lipkin et al, 1999, Ann N Y Acad Sci 889, 14-19). In many important ways, this model system recapitulates the salient steps of colon carcinogenesis and thus represents a useful (and extensively utilized) experimental system. The compound was suspended (35 mg/ml, wt/v) in a solution of 0.5% carboxy methylcellulose (Sigma Chemical Co., St. Louis, Mo.). Six-week-old female C57BL/6J APCMin/+ mice and the corresponding C57BL/6J+/+ wild type mice (of which the Min mice are a congenic derivative) were used. From each type of mouse two groups were prepared, each containing 10 mice. Each mouse was treated via oral administration by gavage as follows: Group 1, wild type controls treated with vehicle; group 2, wild type controls treated with the test compound 100 mg/kg/day; group 3, Min mice treated with vehicle; group 4, Min mice treated with the test compound 100 mg/kg/day. After 21 days of treatment all animals were euthanized and their small intestine was dissected. Tumors were counted under a magnifying lens.

The test compound did not affect the body weight of mice and there was no evidence of gastrointestinal toxicity: there was no statistically significant difference in the body weights of the four groups of mice at either the beginning or the end of the study (see Table below), nor during its course. At necropsy, there was no evidence of gastric or other gastrointestinal toxicity such as mucosal hyperemia, erosions, ulcers or bleeding. No other toxicity was noted upon examination of abdominal organs. All data in mean±SD

| | Body Weight, g | |
|---|---|---|
| Group (N) | Start | End |
| Wild type | | |
| Vehicle (10) | 15.2 ± 0.3 | 17.1 ± 0.4 |
| Compound 5 (10) | 14.8 ± 0.4 | 16.7 ± 0.3 |
| Min | | |
| Vehicle (10) | 15.5 ± 0.5 | 17.3 ± 0.2 |
| Compound 5 (10) | 15.1 ± 0.5 | 17.3 ± 0.3 |

Figure 8:
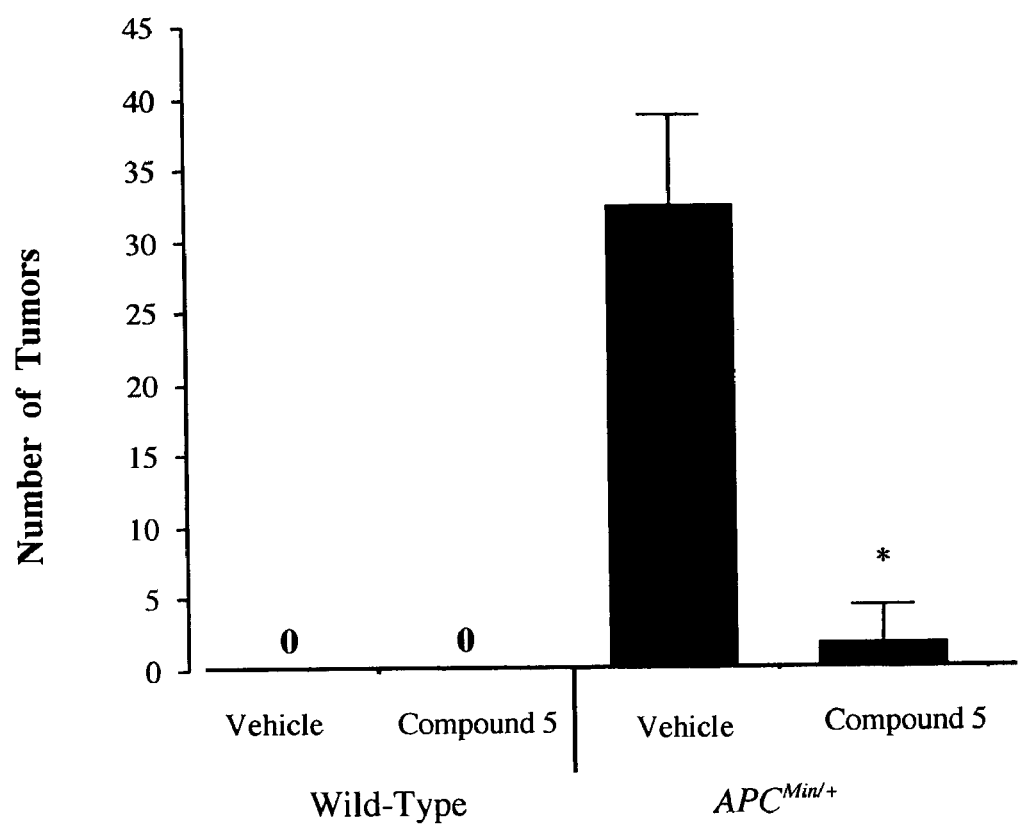
FIG. 8 shows the effect of compound 5 on tumor growth in an animal model of colon cancer.

The compound reduced the number of tumors by 95.6% (number of tumors in controls=32.1±6.4; number of tumors in treated animals=1.4±2.8, p<0.001, N=10 per group; values are mean±SD) (see FIG. 8). The small intestine is the part of the gastrointestinal tract where by far the greatest number of tumors develops in this animal tumor model. As expected, no tumors were observed in any of the wild type animals. Additionally, the few tumors seen in Min mice treated with the compound were on inspection far smaller than those observed in Min mice treated with vehicle alone. The genotype of the animals was confirmed by the polymerase chain reaction testing the mutation in the Apc gene.

This invention may be embodied in other forms or carried out in other ways without departing from the spirit or essential characteristics thereof. The present disclosure is therefore to be considered as in all aspects illustrative and not restrictive, and all changes which come within the meaning and range of equivalency are intended to be embraced therein.

Various references are cited throughout this specification, each of which is incorporated herein by reference in its entirety.

What is claimed is:

1. A compound of Formula I

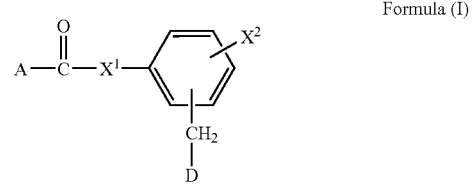

Formula (I)

or a tautomer thereof, or a ester thereof;

wherein $X^1$ is selected from the group consisting of —O— and —NH—;

wherein $X^2$ is one or more substituents independently selected from the group consisting of hydrogen, halogen, hydroxyl, —$NO_2$, —$ONO_2$, —CN; an optionally substituted aliphatic, alicyclic, heteroaliphatic, aromatic, heterocyclic, heteroaromatic moiety; —$OR^R$, —$S(=O)_nR^d$, —$NR^bR^c$, —$C(=O)R^a$, and —$C(=O)OR^a$, wherein n is 0-2, $R^R$ is an optionally substituted aliphatic, alicyclic, heteroaliphatic, heterocyclic, aromatic, heteroaromatic or acyl moiety; $R^a$, for each occurrence, is independently hydrogen or an optionally substituted aliphatic, alicyclic, heteroaliphatic, heterocyclic, aromatic, or a heteroaromatic moiety; $R^b$ and $R^c$, for each occurrence, are independently selected from the group consisting of hydrogen; hydroxy; $SO_2R^d$; aliphatic, alicyclic, heteroaliphatic, heterocyclic, aromatic, heteroaromatic or an acyl moiety; $R^d$, for each occurrence, is independently selected from the group consisting of hydrogen; —$N(R^e)_2$; aliphatic, aryl and heteroaryl; and $R^e$, for each occurrence, is independently hydrogen or aliphatic;

wherein A is

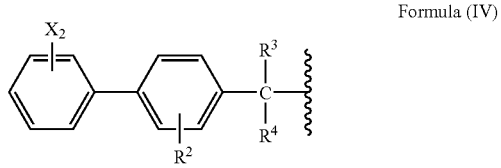

Formula (IV)

wherein $R^2$ is at least one halogen, $X^2$ is as defined above and $R^3$ and $R^4$ are independently hydrogen or an aliphatic group, wherein D is hydroxyl; nitrate; halide; tosylate; phosphate; —$OSO_2NR_xR_y$, where $R_x$ and $R_y$ are independently hydrogen, or an aliphatic, alicyclic, heteroaliphatic, heterocyclic, aromatic, heteroaromatic or acyl moiety; —O—$C_6H_4OC(=O)CH_3$; an alkoxy moiety; an acyl moiety; or

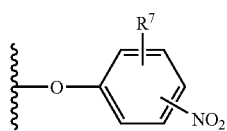
Formula (II)
where R⁷ is hydrogen or one or more nitro groups;
with the proviso that the compound does not have the following structure
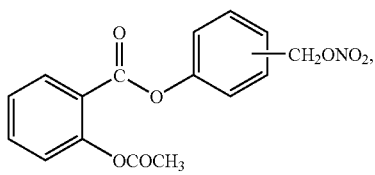
and that when $X_1$ is O and $X_2$ is H, D is not nitrate.
2. The compound of claim 1 wherein the compound is selected from the group consisting of:
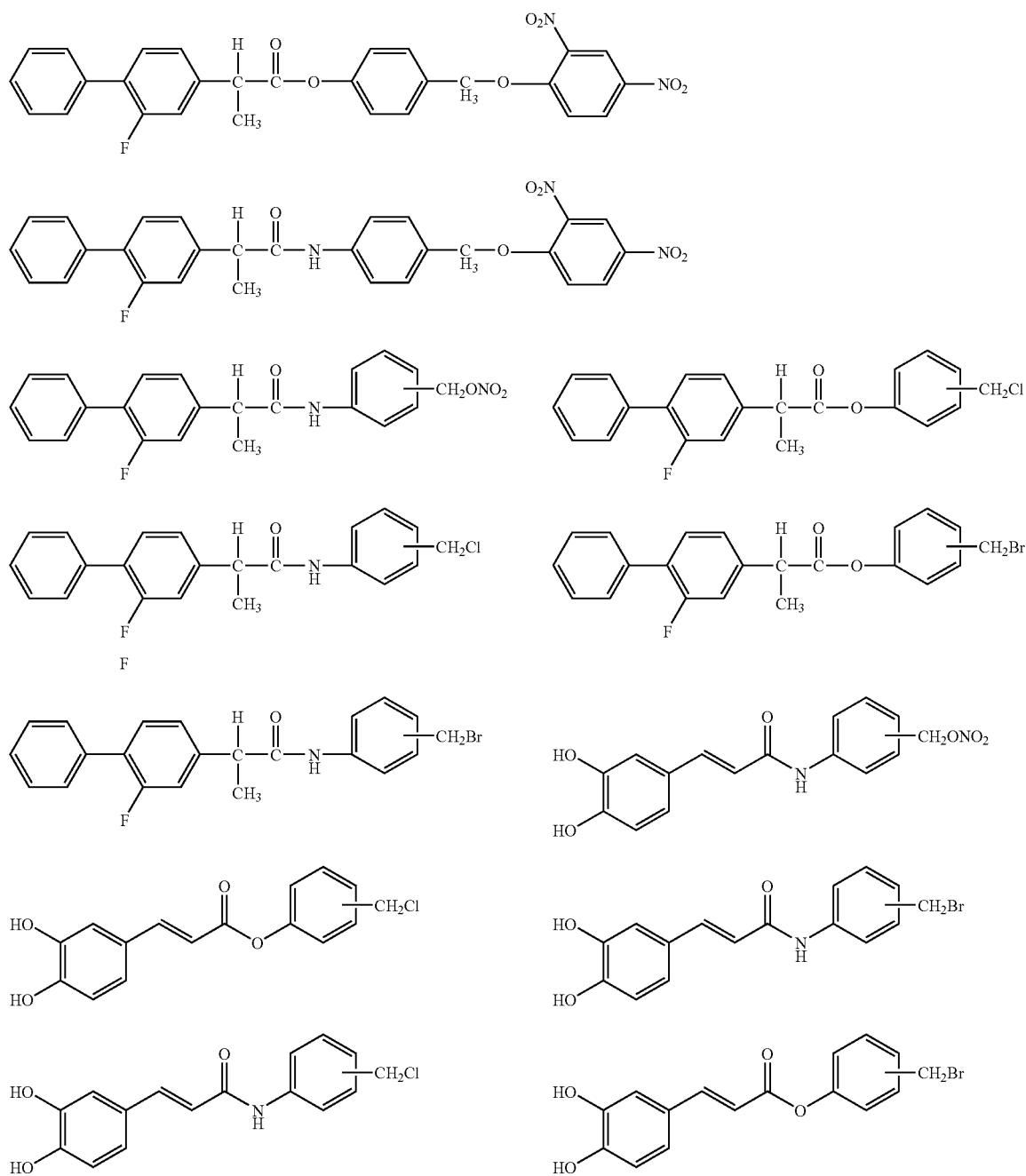

51
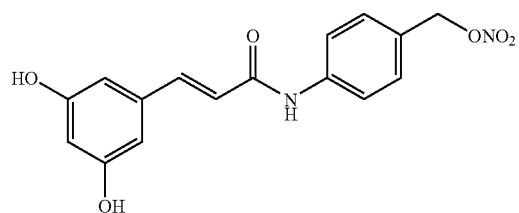
-continued
52
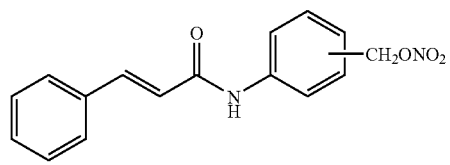
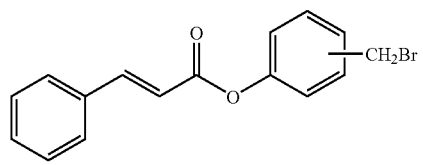
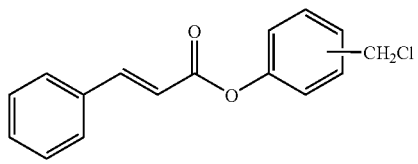
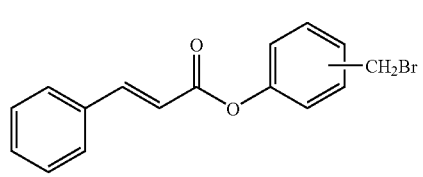
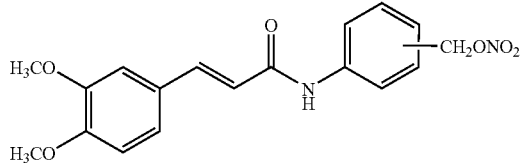
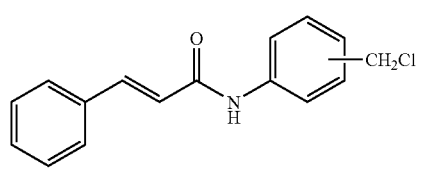
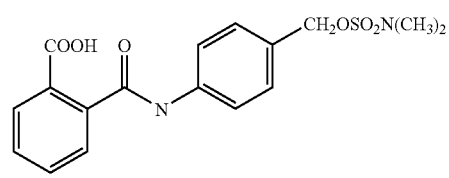
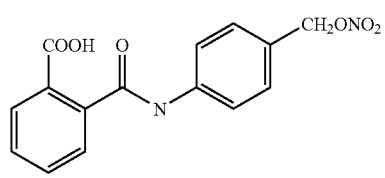
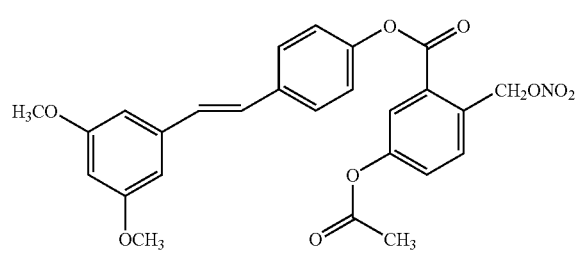
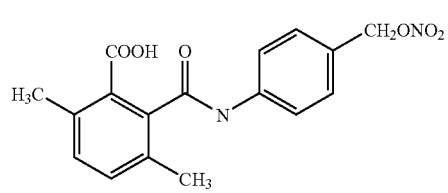
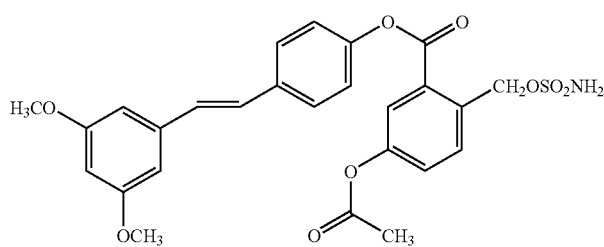
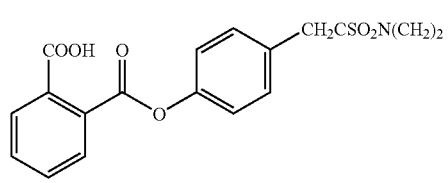
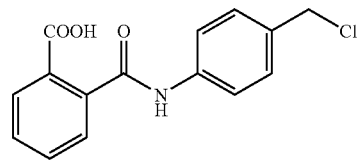
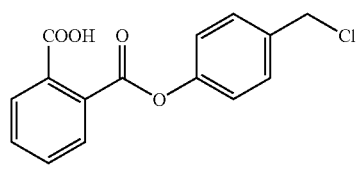

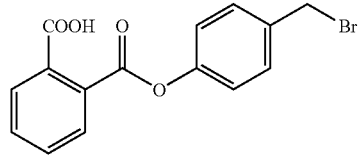

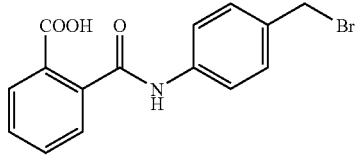

and a meta-, ortho-, or para-isomer from among:

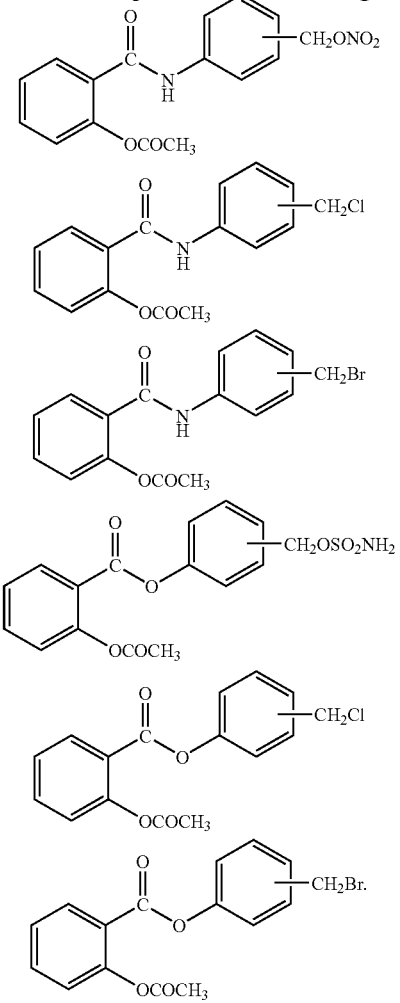

3. A composition comprising the compound of claim 1 and a carrier or excipient.

4. A compound of Formula I

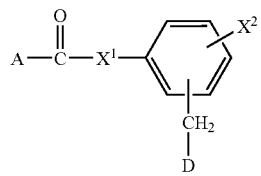

Formula (I)

or a tautomer thereof, or a ester thereof;

wherein $X^1$ is —NH—;

wherein $X^2$ is one or more substituents independently selected from the group consisting of hydrogen, halogen, hydroxyl, —$NO_2$, —$ONO_2$, —CN; an optionally substituted aliphatic, alicyclic, heteroaliphatic, aromatic, heterocyclic, heteroaromatic moiety; —$OR^R$, —$S(=O)_nR^d$, —$NR^bR^c$, —$C(=O)R^a$ and —$C(=O)OR^a$, wherein n is 0-2, $R^R$ is an optionally substituted aliphatic, alicyclic, heteroaliphatic, heterocyclic, aromatic, heteroaromatic or acyl moiety; $R^a$, for each occurrence, is independently hydrogen or an optionally substituted aliphatic, alicyclic, heteroaliphatic, heterocyclic, aromatic, or a heteroaromatic moiety; $R^b$ and $R^c$, for each occurrence, are independently selected from the group consisting of hydrogen; hydroxy; $SO_2R^d$; aliphatic, alicyclic, heteroaliphatic, heterocyclic, aromatic, heteroaromatic or an acyl moiety; $R^d$, for each occurrence, is independently selected from the group consisting of hydrogen; —$N(R^e)_2$; aliphatic, aryl and heteroaryl; and $R^e$, for each occurrence, is independently hydrogen or aliphatic;

wherein A is an optionally substituted aliphatic, alicyclic, heteroaliphatic, heterocyclic, aromatic, or heteroaromatic group;

wherein D is hydroxyl; halide; tosylate; phosphate; —$OSO_2NR_xR_y$, where $R_x$ and $R_y$ are independently hydrogen, or an aliphatic, alicyclic, heteroaliphatic, heterocyclic, aromatic, heteroaromatic or acyl moiety; —O—$C_6H_4OC(=O)CH_3$; an alkoxy moiety; an acyl moiety; or

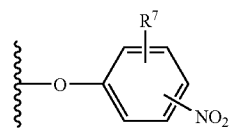

Formula (II)

where $R^7$ is hydrogen or one or more nitro groups.

* * * * *